United States Patent
Roques et al.

(10) Patent No.: US 9,388,129 B2
(45) Date of Patent: Jul. 12, 2016

(54) MIXED INHIBITORS OF AMINOPEPTIDASE N AND NEPRILYSIN

(71) Applicant: PHARMALEADS, Paris (FR)

(72) Inventors: Bernard Pierre Roques, Paris (FR); Marie-Claude Fournie-Zaluski, Paris (FR); Hervé Poras, Bailly (FR)

(73) Assignee: PHARMALEADS, Paris (FR)

( * ) Notice: Subject to any disclaimer, the term of this patent is extended or adjusted under 35 U.S.C. 154(b) by 0 days.

(21) Appl. No.: 14/437,979

(22) PCT Filed: Oct. 23, 2013

(86) PCT No.: PCT/EP2013/072203
§ 371 (c)(1),
(2) Date: Apr. 23, 2015

(87) PCT Pub. No.: WO2014/064166
PCT Pub. Date: May 1, 2014

(65) Prior Publication Data
US 2015/0299116 A1    Oct. 22, 2015

(30) Foreign Application Priority Data
Oct. 23, 2012  (FR) ..................... 12 60097

(51) Int. Cl.
*A61P 25/00* (2006.01)
*C07C 321/14* (2006.01)
*C07C 323/56* (2006.01)
*C07C 323/61* (2006.01)
*A61K 31/216* (2006.01)
*A61K 31/221* (2006.01)
*A61K 31/27* (2006.01)
*A61K 45/06* (2006.01)

(52) U.S. Cl.
CPC ............. *C07C 321/14* (2013.01); *A61K 31/216* (2013.01); *A61K 31/221* (2013.01); *A61K 31/27* (2013.01); *A61K 45/06* (2013.01); *C07C 323/56* (2013.01); *C07C 323/61* (2013.01); *C07C 2101/08* (2013.01); *C07C 2101/14* (2013.01); *C07C 2101/16* (2013.01); *C07C 2102/08* (2013.01)

(58) Field of Classification Search
USPC .......................... 514/1.1, 1.3, 18.3, 18.4, 18.5
See application file for complete search history.

(56) References Cited

U.S. PATENT DOCUMENTS

| | | | |
|---|---|---|---|
| 4,618,708 A | 10/1986 | Roques et al. | |
| 4,738,803 A | 4/1988 | Roques et al. | |
| 5,491,169 A | 2/1996 | Roques et al. | |
| 6,391,866 B1 | 5/2002 | Roques et al. | |
| 6,518,260 B1 | 2/2003 | Fournie-Zaluski et al. | |
| 7,875,436 B2 | 1/2011 | Fournie-Zaluski et al. | |
| 8,247,608 B2 | 8/2012 | Roques et al. | |
| 8,247,609 B2 * | 8/2012 | Roques ................. C07C 323/52 564/340 |
| 8,466,309 B2 | 6/2013 | Fournie-Zaluski et al. | |
| 2009/0131509 A1 | 5/2009 | Roques et al. | |
| 2011/0071218 A1 | 3/2011 | Fournie-Zaluski et al. | |
| 2011/0124601 A1 | 5/2011 | Roques et al. | |
| 2014/0161839 A1 | 6/2014 | Roques et al. | |

FOREIGN PATENT DOCUMENTS

| | | | |
|---|---|---|---|
| FR | 2605004 A1 | 4/1988 | |
| FR | 2869908 A1 | 11/2005 | |
| WO | WO-2004/048394 A1 | 6/2004 | |
| WO | WO-2007/048787 A1 | 5/2007 | |

OTHER PUBLICATIONS

Aubrey, Muriel, et al.; "The use of a monoclonal antibody for the rapid purification of kidney neutral endopeptidase ("enkephalinase") solubilized in octyl glucoside," Biochem. Cell Biol., vol. 65, 1987, pp. 398-404.

Barcelo, Gérard, et al.; "Alkyl 1-Chloroalkyl Carbonates: Reagents for the Synthesis of Carbamates and Protection of Amino Groups," Papers, Aug. 1986, pp. 627-632.

Chen, Ping, et al.; "A Practical Method for the Preparation of α'-Chloroketones of N-Carbamate Protected-α-Aminoacids," Tetrahedron Letters, vol. 38, No. 18, 1997, pp. 3175-3178.

Claeson, Göran, et al.; "1,2-Dithiolane-3-carboxylic Acid," Acta Chemica Scandinavica, 22, No. 10, 1968, pp. 3155-3159.

Cundy, Kenneth C., et al.; "[(±)-1-([α-Isobutanoyloxyethoxy)carbonyl]aminomethyl)-1-cyclohexane Acetic Acid], A Novel Gabapentin Prodrug: 1. Design, Synthesis, Enzymatic Conversion to Gabapentin, and Transport by Intestinal Solute Transporters," The Journal of Pharmacology and Experimental Therapeutics, vol. 311, No. 1, 2004, pp. 315-323.

Dutta, Anand S., et al.; "Inhibitors of Human Leucocyte Elastase. Peptides Incorporating an α-Azanorvaline Residue or a Thiomethylene Linkage in Place of a Peptide Bond," J. Chem. Soc. Perkin Trans., Jan. 1, 1987, pp. 111-120.

Eddy, Nathan B., et al.; "Synthetic Analgesics. II. Dithienylbutenyl- and Dithienylbutylamines," National Institute of Arthritis and Metabolic Diseases, National Institutes of Health, received for publication Nov. 3, 1952, pp. 385-393.

Goudreau, Nathalie, et al.; Dns-Gly-(p-NO$_2$)Phe-βAla, a Specific Fluorogenic Substrate for Neutral Endopeptidase 24.11, Analytical Biochemistry, 219, 1994, pp. 87-95.

Harris, Katharine M., et. al.; "Studies on deprotection of cysteine and selenocysteine side-chain protecting groups," Journal of Peptide Science, 13, 2007, pp. 81-93.

(Continued)

*Primary Examiner* — Pancham Bakshi
(74) *Attorney, Agent, or Firm* — Harness, Dickey & Pierce, P.L.C.

(57) ABSTRACT

Mixed inhibitors of aminopeptidase N and neprilysin are disclosed. Pharmaceutical compositions containing at least one of these compounds, used alone or in combination with morphine and derivatives thereof, endocannabinoids and inhibitors of endocannabinoid metabolism, GABA derivatives such as gabapentin or pregabalin, duloxetine or methadone, can be used as an analgesic, anxiolytic, antidepressant or anti-inflammatory.

22 Claims, 1 Drawing Sheet

(56) References Cited

OTHER PUBLICATIONS

Le Guen, Stéphanie, et al.; "Pain management by a new series of dual inhibitors of enkephalin degrading enzymes: long lasting antinociceptive properties and potentiation by $CCK_2$ antagonist or methadone," Pain, 104, 2003, pp. 139-148.

Nieto, Magdalena Mas, et al.; "Facilitation of enkephalins catabolism inhibitor-induced antinociception by drugs classically used in pain management," Neuropharmacology, 41, 2001, pp. 496-506.

Noble, Florence, et al.; "Protection of endogenous enkephalin catabolism as natural approach to novel analgesic and antidepressant drugs," Expert Opin. Ther. Targets, 11(2), 2007, pp. 145-159.

Valverde, Olga, et al.; "$\Delta^9$-tetrahydrocannabinol releases and facilitates the effects of endogenous enkephalins: reduction in morphine withdrawal syndrome without change in rewarding effect," European Journal of Neuroscience, vol. 13, 2001, pp. 1816-1824.

Roques, Bernard P. et al: "Inhibiting the breakdown of endogenous opioids and cannabinoids to alleviate pain", Nature Review Drug Discovery, vo. 11, No. 4, 1 Apr. 1, 2012, pp. 292-310, XP055071274, ISSN: 1474-1776; DOI:10.1038/nrd3673 "Heterodisulphide DENK inhibitors"; p. 299; figure 3.

Noble, Florence et al.: Pain-suppressive effects on various nociceptive stimuli (thermal, chemical, electrical and inflammatory) of the first orally active enkephalin-metabolizing enzyme inhibitor RB 120, Pain, Elsevier Science Publishers, Amsterdam, NL, vol. 73, No. 3, Jan. 1, 1997 pp. 383-391, XP 002386725, ISSN: 0304-3959, DOI: 10.1016/S0304-3959(97) 00125-5, p. 386; table 1.

Fournie-Zaluski, M-C et al: "Mixed Inhibitor—Prodrug As a New Approach Toward Systemically Active Inhibitors of Enkephalin-Degrading Enzymes", Journal of Medicinal Chemistry, American Chemical Society, US, vol. 35, No. 13, Jan. 1, 1992, pp. 2473-2481, XP002019768, ISSN: 0022-2623, DOI: 10.1021/JM00091A016 p. 2477; table II.

Noble F et al: "Inhibition of the Enkephalin-Metabolizing Enzymes by the First Systemically Active Mixed Inhibitor Prodrug RB 101—Induces Potent Analgesic Responses in Mice and Rats", Journal of Pharmacology and Experimental Therapeutics, American Society for Pharmacology and Experimental Therapeutics, US, vol. 261, No. 1, Jan. 1, 1992, pp. 181-190, XP000386321, ISSN:0022-3565 p. 183; table 1.

Mosnaim, Aron David et al: In Vitro Methionine[5]-Enkephalin Degradation Kinetics by Human Brain Preparations, Neurochem Res (2008) 33:81-86, DOI 10.1007/s11064-007-9418-6, published online: Aug. 4, 2007.

Roques, Bernard P. et al: Neutral Endopeptidase 24.11: Structure, Inhibition, and Experimental and Clinical Pharmacology, Pharmacol. Rev., vol. 45, No. 1, 87-146, (1993).

Wisner, Anne et al: "Human Opiorphin, a natural antinociceptive modulator of opioid-dependent pathways", PNAS (2006), vol. 103, No. 47, 17979-17984; DOI:10.1073/pnas.0605865103, Nov. 21, 2006.

Menendez, Luis et al: "Inhibition of osteosarcoma-induced thermal hyperalgesia in mice by the orally active dual enkephalinase inhibitor PL37. Potentiation by gabapentin", Eur. J. Pharmacol,. 596, pp. 50-55, Elsevier (2008) available online Jul. 30, 2008.

Thibault, Karine et al: Antinociceptive and anti-allodynic effects of oral PL37, a complete inhibitor of enkephalin-catabolizing enzymes, in a rat model of peripheral neuropathic pain induced by vincristine, Eur J. Pharmacol, 600, pp. 71-77, Elsevier B.V. (2008) available online Oct. 2008.

* cited by examiner

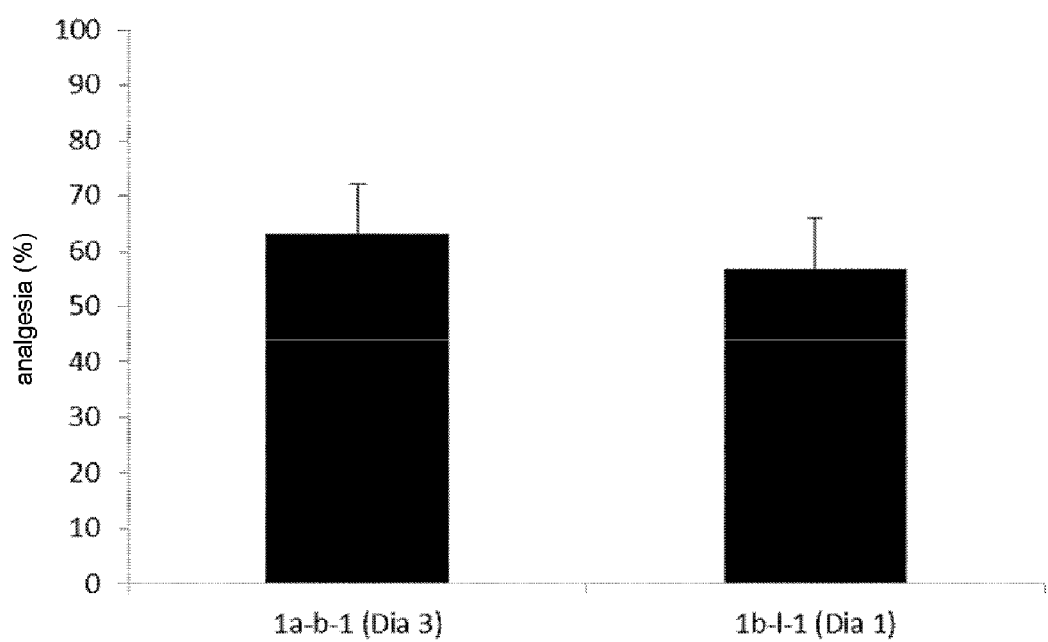

MIXED INHIBITORS OF AMINOPEPTIDASE N AND NEPRILYSIN

CROSS-REFERENCE TO RELATED APPLICATIONS

This application is a National Phase Entry of International Application No. PCT/EP2013/072203, filed on Oct. 23, 2013, which claims priority to French Patent Application Serial No. 1260097, filed on Oct. 23, 2012, both of which are incorporated by reference herein.

TECHNICAL FIELD

The invention relates to mixed inhibitors of aminopeptidase N and neprilysin, enzymes involved in the degradation of enkephalins.

BACKGROUND

Enkephalins, Tyr-Gly-Gly-Phe-Met(Leu), are endogenous ligands of opioid receptors μ and δ and are involved in the regulation of nociceptive impulses in the central and peripheral nervous systems. However, administered intracerebroventricularly in rodents, these peptides induce only a very brief analgesic response due to their very rapid inactivation in vivo, including in man (Mosnaim et al. (2008) *Neurochem. Res.*, 33, 81-86), although their affinity for opioid receptors is similar to that of morphine. Two metallopeptidases are responsible for this inactivation: aminopeptidase N (APN, EC 3.4.11.2) and neprilysin (NEP, EC 3.4.24.11), which cleave, respectively, the $Tyr^1$-$Gly^2$ bond and the $Gly^3$-$Phe^4$ bond of enkephalins, thus resulting in inactive metabolites (Roques et al. (1993) *Pharmacol. Rev.*, 45, 87-146).

Mixed inhibitors of these two enzymes are known, which by completely protecting endogenous enkephalins from their enzymatic degradation show the pharmacological activities, in particular the analgesic and antidepressant activities, of enkephalins (Noble et al. (2007) *Expert. Opin. Ther. Targets*, 11, 145-149). These inhibitors, disclosed in the prior art, include hydroxamates (FR2518088 and FR2605004), aminophosphinic compounds (FR2755135, FR2777780, FR0855015), amino acid derivatives with a thiol functional group (FR2651229, FR0510862, FR0604030, FR0853092), endogenous peptides (Wisner et al. *PNAS* (2006), 103, 17979-17984). These various molecules have physicochemical properties (solubility) and pharmacodynamic properties (bioavailability) that bestow upon them pharmacological effectiveness, intravenously or orally, on different types of pain, in particular acute or chronic pain with excess nociception (Noble et al. (2007) *Expert. Opin. Ther. Targets*, 11, 145-149) and neuropathic pain (Menendez et al. (2008) *Eur J Pharmacol*, 596, 50-55; Thibault et al. (2008) *Eur. J. Pharmacol.*, 600, 71-77). However, none of the mixed inhibitors disclosed to date makes it possible to obtain an analgesic response that is rapid, intense and with a sufficiently long duration of action in the case of sharp pain (post-operative, cancer, traumatic, dental, etc.) after intravenous administration, at low doses enabling use in extended perfusion in a clinically suitable vehicle.

The objective of the invention is to provide compounds having the beneficial properties of morphine substances on the central nervous system, in particular analgesia, behavioral effects (reduction in the emotional component of pain and antidepressant responses) without their major disadvantages for the central nervous system (habituation, physical and psychic dependence, respiratory depression) and the peripheral nervous system (constipation). In addition, it will be advantageous that the compounds have beneficial peripheral effects (anti-inflammatory and anti-neuropathic) without the disadvantages stated above.

SUMMARY

The invention relates to compounds having the following general formula (I):

$$R-NH-CH(R_1)-CH_2-S-S-C(R_2)(R_3)-COCH_2-CH(R_4)-COR_5 \text{ with } R, R_1, R_2, R_3, R_4 \text{ et } R_5 \text{ as defined hereinafter.} \quad (1)$$

The invention also relates to pharmaceutical compositions containing at least one compound of the present invention. The invention also relates to pharmaceutical compositions containing at least one compound of the present invention and at least one compound selected from morphine and derivatives thereof, endocannabinoids and inhibitors of endocannabinoid metabolism, GABA derivatives such as gabapentin or pregabalin, duloxetine or methadone. Finally, the invention relates to compounds of the present invention or pharmaceutical compositions containing same used as an analgesic, anxiolytic, antidepressant or anti-inflammatory.

BRIEF DESCRIPTION OF THE DRAWING

FIG. 1: antinociceptive response induced after intravenous injection of compounds according to the present invention (10 mg/kg)—Hot plate test with mice.

DETAILED DESCRIPTION

Alkyl groups designate linear or branched C1, C2, C3, C4, C5 or C6 hydrocarbon chains, in particular methyl, ethyl, n-propyl, i-propyl, n-butyl, i-butyl or t-butyl radicals. Examples of aromatic or saturated 5- or 6-atom heterocycles, comprised of at least one sulfur, oxygen or nitrogen atom, include the following radicals: thienyl, pyrrolyl, imidazoyl, pyrazolyl, isothiazolyl, pyridyl, pyrazinyl, pyrimidinyl, pyridazinyl, pyrrolidinyl, pyrrolinyl, imidazolidinyl, pyrazolidinyl, pyrazolinyl, piperidyl, piperazinyl, thiadiazolyl, furyl, pyranyl, isoxazolyl, morpholinyl, furazanyl, oxazolyl, oxazolidinyl and oxazolinyl. The term "halogen" as designated herein refers to chlorine, bromine, iodine or fluorine.

The compounds of the present invention correspond to the association, via a disulfide bridge, of an APN inhibitor and a NEP inhibitor, capable of inhibiting the activity of these two enzymes at nanomolar concentrations. This disulfide bridge is cleaved in vivo and releases the two inhibitors which will interact with their respective target (NEP or APN) (Fournié-Zaluski et al. (1992) *J. Med. Chem.*, 35, 2473-2481).

The NEP inhibitors disclosed to date generally have a peptide motif and thus one or more amide bonds. For example, peptidomimetic derivatives containing at least one amide bond and further containing a disulfide motif were disclosed in articles by Roques et al. (*Nature Rev. Drug Discov.* (2012) 11, 292-311), Noble et al. 1992 (*Journal of Pharmacology and Experimental Therapeutics* 261 (1992), 1, 181-190), Noble et al. 1997 (*Pain* 73 (97), 383-391), and in patent documents WO 2009/138436 and FR 2892413. Furthermore, they generally have a molecular weight (MW) greater than 500 Da. These characteristics are not very favorable to the crossing of physiological barriers, such as the intestinal barrier, for example, and as a result these products have a rather low oral bioavailability. The same is true for the crossing of the blood-brain barrier.

The structure of the NEP inhibitors useful in the present invention and making it possible to overcome these disadvantages is characterized by: i) a novel thioketone motif capable of interacting with the zinc of the NEP in a monodentate or bidentate fashion, ii) an absence of the peptide motif (thus lacking an amide bond), iii) a skeleton comprising a minimum of groups making it possible to achieve a nanomolar affinity for NEP, iv) a low molecular weight.

The compounds of the present invention have the following general formula (1):

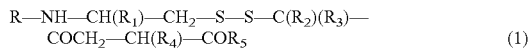

$$R-NH-CH(R_1)-CH_2-S-S-C(R_2)(R_3)-COCH_2-CH(R_4)-COR_5 \quad (1)$$

wherein R is:
a) R is:
  hydrogen;
  an alkoxyalkylcarbonyl group R'C(O)OCH(R")OC(O)— where R' and R" are, independently, an alkyl group containing 1 to 6 carbon atoms;
b) $R_1$ is a linear or branched alkyl group of 1 to 6 carbon atoms, substituted, or not, by an —OR''', —SOR''' or —SR''' group, with R''' being an alkyl group of 1 to 6 carbon atoms, substituted or not, by one or more halogen atoms;
c) $R_2$ is:
  a linear or branched alkyl group of 1 to 6 carbon atoms, substituted or not, by:
    an —$OR_6$, —$SR_6$ or —$SOR_6$ group, with $R_6$ being hydrogen, a linear or branched alkyl group of 1 to 4 carbons, a phenyl or benzyl group;
    a —$CO_2R_7$ group, with $R_7$ being hydrogen, a linear or branched alkyl group comprised of 2 to 4 carbon atoms, or a benzyl group;
    an —$NR_8R_9$ group, with $R_8$ and $R_9$ being, independently, hydrogen, a linear or branched alkyl group of 1 to 4 carbon atoms, a phenyl or benzyl group, or with —$NR_8R_9$ taken together being a saturated 5- or 6-membered heterocycle comprising one or more heteroatoms selected from N or O, preferably being a morpholine or a piperidine; or
    a carboxamide group —$CONR_8R_9$, with —$NR_8R_9$ as defined above;
    a phenyl group, substituted, or not, by one or more halogens selected from fluorine or bromine, an alkoxy group —$OR_6$, with $R_6$ having the same definition as above, or by a phenyl group;
    an aromatic 5- or 6-membered heterocycle comprising 1 or 2 heteroatoms selected from oxygen, nitrogen and sulfur;
    a saturated 5- or 6-member cyclic or heterocyclic compound comprised of 1 or 2 heteroatoms selected from oxygen, nitrogen and sulfur;
  a saturated 5- or 6-membered cyclic or heterocyclic compound comprising 1 or 2 heteroatoms selected from oxygen, nitrogen and sulfur; or
  a phenyl group, substituted or not, by one or more halogens selected from fluorine or bromine, or by an —$OR_5$ group with $R_5$ having the same definition as above;
  and $R_3$ is hydrogen; or
  $R_2$ and $R_3$ are identical and are a linear or branched alkyl group of 1 to 6 carbon atoms; or
  —$C(R_2)(R_3)$— taken together is:
    a saturated 5-membered cyclic compound fused, or not, to an aromatic ring (leading to, for example, the indanyl ring);
    a saturated 6-membered cyclic compound;
    a saturated 6-membered heterocyclic compound comprising 1 heteroatom, at the 4-position, selected from oxygen, nitrogen and sulfur, wherein when the heteroatom is nitrogen, the nitrogen is substituted, or not, by an alkyl group of 1 to 6 carbon atoms, a phenyl, benzyl or alkanoyl group;
d) $R_4$ is:
  a linear or branched alkyl group of 1 to 6 carbon atoms, substituted or not, by:
    an —$OR_6$, —$SR_6$ or —$SOR_6$ group, with $R_6$ being hydrogen, a linear or branched alkyl group of 1 to 4 carbons, a phenyl or benzyl group;
    a —$CO_2R_7$ group, with $R_7$ being hydrogen, a linear or branched alkyl group comprised of 2 to 4 carbon atoms, a benzyl group;
    an —$NR_8R_9$ group, with $R_8$ and $R_9$ being, independently, hydrogen, a linear or branched alkyl group of 1 to 4 carbon atoms, a phenyl or benzyl group, or with —$NR_8R_9$ taken together being a saturated 5- or 6-member heterocycle comprising one or more heteroatoms selected from N or O, preferably being a morpholine or a piperidine;
    a carboxamide group —$CONR_8R_9$, with —$NR_8R_9$ as defined above;
    a phenyl group substituted, or not, by:
      one or more halogens selected from fluorine or bromine;
      an —$OR_6$ group, $R_6$ having the same definition as above;
      a phenyl or thienyl group;
      an aromatic 5- or 6-membered heterocycle comprising 1 or 2 heteroatoms selected from oxygen, nitrogen and sulfur; or
      a saturated 5- or 6-membered cyclic or heterocyclic compound comprising 1 or 2 heteroatoms selected from oxygen, nitrogen and sulfur;
    a phenyl group, substituted, or not, by:
      one or more halogens, notably fluorine or bromine;
      an —$OR_6$ group, with $R_6$ having the same definition as above;
      a phenyl;
      an aromatic 5- or 6-membered heterocycle comprising 1 or 2 heteroatoms selected from oxygen, nitrogen and sulfur;
e) $R_5$ is:
  a hydroxyl group;
  an —$NR_8R_9$ group, with $R_8$ and $R_9$ being, independently, hydrogen, a linear or branched alkyl group of 1 to 4 carbon atoms, a phenyl or benzyl group, or with —$NR_8R_9$ taken together being a 5- or 6-membered heterocycle, comprising one or more heteroatoms selected from N or O, preferably being a morpholine or a piperidine;
  an alkoxy group —$OR_{10}$, with $R_{10}$ being:
    a linear or branched alkyl group, comprised of 2 to 6 carbon atoms;
    a benzyl group;
    a —$CHR_{11}$—$COOR_{12}$, —$CHR_{11}$—O—$C(=O)R_{12}$, —$CHR_{11}$— or —$C(=O)$—$OR_{12}$ group wherein $R_{11}$ and $R_{12}$ are, independently, a linear or branched alkyl group of 1 to 6 carbon atoms.

The compounds of the present invention can be in the form of pharmacologically acceptable addition salts, such as the addition salts of compounds of formula (1) with inorganic or organic acids when the amine functional group is free, or inorganic or organic bases when the acid functional group is free. Protection of the N-terminal and/or C-terminal parts by R and $R_5$ groups is generally carried out to promote bioavailability by the various routes of administration.

In particular embodiments of the invention, the compounds have the general formula (1) wherein $R_2$ is a linear or branched alkyl group of 1 to 6 carbon atoms or a linear or branched alkyl group of 1 to 6 carbon atoms substituted by:
  a phenyl group;
  a phenyl group substituted by one or more halogens selected from fluorine or bromine;
  an aromatic 5- or 6-membered heterocycle comprising 1 or 2 heteroatoms selected from oxygen, nitrogen and sulfur;
  a saturated 5- or 6-membered cyclic or heterocyclic compound comprising 1 or 2 heteroatoms selected from oxygen, nitrogen and sulfur;
  and $R_3$ is hydrogen; or
$R_2$ and $R_3$ are identical and are a linear or branched alkyl group of 1 to 6 carbon atoms, or
—C($R_2$)($R_3$)— taken together is:
  a saturated 5-membered cyclic compound;
  a saturated 5-membered cyclic compound fused to an aromatic ring;
  a saturated 6-membered cyclic compound; or
  a saturated 6-membered heterocyclic compound comprising 1 heteroatom, at the 4-position, selected from oxygen, nitrogen and sulfur;
and R, $R_1$, $R_4$, $R_5$ are as described above or below.

More particularly, $R_2$ can represent an isobutyl group or a methyl group substituted by:
  a phenyl group;
  a phenyl group substituted at the 4-position by a halogen selected from fluorine or bromine;
  a phenyl group substituted at the 4-position by a phenyl group;
  and $R_3$ is hydrogen, or
$R_2$ and $R_3$ are identical and are a methyl or ethyl group, or
—C($R_2$)($R_3$)— are together:
  a saturated 5- or 6-member cyclic group; or
  a saturated 5-member cyclic group fused to an aromatic ring.

In particular embodiments of the invention, the compounds have the following general formula (1) wherein $R_4$ is a linear or branched alkyl group of 1 to 6 carbon atoms substituted by:
  a phenyl group, substituted or not, by one or more halogens selected from fluorine or bromine, an alkoxy group —$OR_6$, with $R_6$ having the same definition as above, or by a phenyl group;
  an aromatic 5- or 6-membered heterocycle comprising 1 or 2 heteroatoms selected from oxygen, nitrogen and sulfur;
  a saturated 5- or 6-membered cyclic compound;
  a saturated 5- or 6-membered heterocycle cyclic compound comprising 1 or 2 heteroatoms selected from oxygen, nitrogen and sulfur;
and R, $R_1$, $R_2$, $R_3$, $R_5$ are as described above or below.

Advantageously, $R_4$ is a linear or branched alkyl group of 1 to 6 carbon atoms substituted by:
  a phenyl group; or
  a phenyl group substituted by:
    one or more halogens selected from fluorine or bromine;
    a phenyl or thienyl group,
and R, $R_1$, $R_2$, $R_3$, $R_5$ are as described above or below.

More particularly, $R_4$ can represent an alkyl group with one carbon substituted by:
  a phenyl group;
  a phenyl group substituted at the 4-position by a halogen selected from fluorine or bromine;
  a phenyl group substituted at the 4-position by a phenyl group.

In particular embodiments of the invention, the compounds have the general formula (1) wherein $R_5$ is:
  a hydroxyl group; or
  an alkoxy group —$OR_{10}$, with $R_{10}$ being:
    a linear or branched alkyl group, comprised of 2 to 6 carbon atoms;
    a benzyl group;
  a —$CHR_{11}$—$COOR_{12}$, —$CHR_{11}$—O—C(=O)$R_{12}$, —$CHR_{11}$— or —C(=O)—$OR_{12}$ group wherein
  $R_{11}$ and $R_{12}$ are, independently, a linear or branched alkyl group of 1 to 6 carbon atoms;
and R, $R_1$, $R_2$, $R_3$, $R_4$ are as described above or below.

Advantageously, $R_5$ is a hydroxyl group and R, $R_1$, $R_2$, $R_3$, $R_4$ are as described above or below.

Preferred compounds have the following general formula (1) wherein
  a) $R_1$ is selected from —$CH_2CH_2SCH_3$, —$CH_2CH_2CH_2CH_3$, $CH_2CH_2SOCH_3$;
  b) $R_2$ is a linear or branched alkyl group of 1 to 6 carbon atoms or a linear or branched alkyl group of 1 to 6 carbon atoms substituted by:
    a phenyl group;
    a phenyl group substituted by one or more halogens selected from fluorine or bromine;
    an aromatic 5- or 6-membered heterocycle comprising 1 or 2 heteroatoms selected from oxygen, nitrogen and sulfur;
    a saturated 5- or 6-membered cyclic or heterocyclic compound comprising 1 or 2 heteroatoms selected from oxygen, nitrogen and sulfur;
    and $R_3$ is hydrogen; or
  $R_2$ and $R_3$ are identical and are a linear or branched alkyl group of 1 to 6 carbon atoms; or
  —C($R_2$)($R_3$)— taken together is:
    a saturated 5-membered cyclic compound;
    a saturated 5-membered cyclic compound fused to an aromatic ring;
    a saturated 6-membered cyclic compound; or
    a saturated 6-membered heterocyclic compound comprising 1 heteroatom, at the 4-position, selected from oxygen, nitrogen and sulfur;
  c) $R_4$ is a linear or branched alkyl group of 1 to 6 carbon atoms substituted by:
    a phenyl group; or
    a phenyl group substituted by:
      one or more halogens selected from fluorine or bromine;
      a phenyl or thienyl group;
  d) $R_5$ is a hydroxyl group.

Preferred compounds have the formula (1) wherein:
$R_2$=$CH_2$Ph; $R_3$=H; $R_4$=$CH_2$Ph; or
$R_2$=iBu; $R_3$=H; $R_4$=$CH_2$(4-Br-Ph); or
$R_2$=$CH_2$(4-Br-Ph); $R_3$=H; $R_4$=$CH_2$(4-Br-Ph); or
$R_2$=$CH_2$(4-Br-Ph); $R_3$=H; $R_4$=$CH_2$Ph; or
$R_2$=$CH_2$Ph; $R_3$=H; $R_4$=$CH_2$(4-Br-Ph); or
$R_2$=$CH_2$(4-Ph-Ph); $R_3$=H; $R_4$=$CH_2$(4-Br-Ph); or
$R_2$=$CH_3$; $R_3$=$CH_3$; $R_4$=$CH_2$(4-Br-Ph); or
$R_2$=$C_2H_5$; $R_3$=$C_2H_5$; $R_4$=$CH_2$(4-Br-Ph); or
C($R_2$)($R_3$)=$C_5H_8$; $R_4$=$CH_2$(4-Br-Ph); or
C($R_2$)($R_3$)=$C_6H_{10}$; $R_4$=$CH_2$(4-Br-Ph); or
C($R_2$)($R_3$)=$C_9H_8$; $R_4$=$CH_2$(4-Br-Ph); or
C($R_2$)($R_3$)=$C_6H_{10}$; $R_4$=$CH_2$(4-Ph-Ph); or
C($R_2$)($R_3$)=$C_5H_8$; $R_4$=$CH_2$(4-Br-Ph); or
C($R_2$)($R_3$)=$C_9H_8$; $R_4$=$CH_2$(4-Ph-Ph).

In particular embodiments, the compounds of the present invention have the formula (1) wherein $R_1$ is selected from —$CH_2CH_2SCH_3$, —$CH_2CH_2CH_2CH_3$, —$CH_2CH_2SOCH_3$. In preferred embodiments, the compounds of the present invention have the formula (1) wherein $R_1$ is selected from —$CH_2CH_2SCH_3$, —$CH_2CH_2CH_2CH_3$, —$CH_2CH_2SOCH_3$, and $R_2$=$CH_2Ph$; $R_3$=H; $R_4$=$CH_2Ph$; or
$R_2$=iBu; $R_3$=H; $R_4$=$CH_2$(4-Br-Ph); or
$R_2$=$CH_2$(4-Br-Ph); $R_3$=H; $R_4$=$CH_2$(4-Br-Ph); or
$R_2$=$CH_2$(4-Br-Ph); $R_3$=H; $R_4$=$CH_2Ph$;
$R_2$=$CH_2Ph$; $R_3$=H; $R_4$=$CH_2$(4-Br-Ph); or
$R_2$=$CH_2$(4-Ph-Ph); $R_3$=H; $R_4$=$CH_2$(4-Br-Ph); or
$R_2$=$CH_3$; $R_3$=$CH_3$; $R_4$=$CH_2$(4-Br-Ph); or
$R_2$=$C_2H_5$; $R_3$=$C_2H_5$; $R_4$=$CH_2$(4-Br-Ph); or
$C(R_2)(R_3)$=$C_5H_8$; $R_4$=$CH_2$(4-Br-Ph); or
$C(R_2)(R_3)$=$C_6H_{10}$; $R_4$=$CH_2$(4-Br-Ph); or
$C(R_2)(R_3)$=$C_9H_8$; $R_4$=$CH_2$(4-Br-Ph); or
$C(R_2)(R_3)$=$C_6H_{10}$; $R_4$=$CH_2$(4-Ph-Ph); or
$C(R_2)(R_3)$=$C_5H_8$; $R_4$=$CH_2$(4-Br-Ph); or
$C(R_2)(R_3)$=$C_9H_8$; $R_4$=$CH_2$(4-Ph-Ph).

In other embodiments, the compounds of the present invention have the formula (1) wherein:

$R_1$=$CH_2CH_2SCH_3$; $R_2$=$CH_2CH(CH_3)_2$; $R_3$=H; $R_4$=$CH_2$(4-Br-Ph);
$R_1$=$CH_2CH_2CH_2CH_3$; $R_2$=$CH_2CH(CH_3)_2$; $R_3$=H; $R_4$=$CH_2$(4-Br-Ph);
$R_1$=$CH_2CH_2SOCH_3$; $R_2$=$CH_2CH(CH_3)_2$; $R_3$=H; $R_4$=$CH_2$(4-Br-Ph);
$R_1$=$CH_2CH_2CH_2CH_3$; —$C(R_2R_3)$—=Cyclohexyl; $R_4$=$CH_2$(4-Br-Ph);
$R_1$=$CH_2CH_2SCH_3$; —$C(R_2)(R_3)$—=Cyclohexyl; $R_4$=$CH_2$(4-Ph-Ph); or
$R_1$=$CH_2CH_2CH_2CH_3$; —$C(R_2)(R_3)$—=Cyclohexyl; $R_4$=$CH_2$(4-Ph-Ph);

and R and $R_5$ are as described above.

In particular embodiments of the invention, the compounds of the present invention have the formula (1) wherein R is hydrogen or R is an R'C(O)OCH(R'')OC(O)— group wherein R' is an isopropyl group and R'' a methyl group, and $R_1$, $R_2$, $R_3$, $R_4$ and $R_5$ are as described above.

The compounds of the present invention can be used as a drug. More particularly, the compounds can be employed to prepare pharmaceutical compositions comprising as active ingredient at least one of the compounds described above in combination with at least one pharmaceutically acceptable excipient. Said excipients are selected, according to the dosage form and mode of administration desired, from the typical excipients known to persons skilled in the art.

As the compounds of the present invention jointly inhibit the enzymatic activities responsible for the degradation of enkephalins, they increase their extracellular endogenous rate and, for this reason, prove to be effective analgesics and/or antidepressants. The analgesic effects of the compounds appear on various acute or chronic pains such as neurogenic, neuropathic, neuroinflammatory or nociceptive pain or general pain such as fibromyalgia. Examples of pain include mechanical pain (for example muscle pain, vascular ischemia), phantom limb pain, pain caused by shingles, cancer pain related to cancer itself or to the consequences of treatment, pain associated with inflammatory diseases (for example, arthritis, rheumatoid arthritis, osteoarthritis, gout), pain related to type I diabetes, pain related to migraines, to facial neuralgia, headaches, pain related to peripheral nerve damage (post-operative, for example), dorsal neuralgias, dental pain, pain related to burns, sunburn, bites or stings, pain related to infections, metabolic disorders (diabetes, alcoholism), nerve compression (hernia, carpel tunnel, fibrosis, etc.), fractures, burns, hematomas, cuts and inflammation.

Finally, typically, and advantageously, the compounds of the present invention do not have the major disadvantages of morphine substances (tolerance, physical dependence, respiratory depression, nausea, sedation, constipation, etc.). Thus, the compounds of the present invention and the pharmaceutical compositions containing same can be useful for at least one use selected from the following uses: analgesic, anxiolytic, antidepressant or anti-inflammatory. The present invention also relates to the use of compounds of formula (I) as defined above and pharmaceutical compositions containing same for the manufacture of an analgesic, anxiolytic, antidepressant or anti-inflammatory drug, more particularly a drug for the treatment of pain. The pain can be, notably, chronic or acute pain as defined above. The compounds of the present invention can be used alone or in combination with compounds known for their antinociceptive properties. This combination can enable a potentiation of pharmacological effects, as known antinociceptive compounds at high doses generally have undesirable side effects.

Such potentiation (synergy) of pharmacological effects has been shown in the past by combining mixed inhibitors having a chemical structure different from that of the mixed inhibitors of the present invention with known antinociceptive compounds. Thus, strong potentiation of antinociceptive responses was obtained, for example, in combination with: morphine (Mas Nieto et al. (2001) *Neuropharmacol.* 41, 496-506, THC (Valverde et al. (2001) *Eur. J. Neurosci.*, 13, 1816-1824), gabapentin (Menendez et al. (2007) *Eur. J. Pharmacol.*, 596, 50-55) and analogues thereof such as pregabalin. These combinations make it possible, for an equivalent pharmacological effect, to reduce by 3 to 10 times the doses of the components of the combination (morphine and inhibitor, for example).

Thus, in one embodiment, the pharmaceutical compositions comprise as active ingredient at least one of the compounds of the present invention in combination with at least one antinociceptive agent and at least one pharmaceutically acceptable excipient. The antinociceptive agents can be selected from:
  morphine and derivatives thereof,
  endocannabinoids, $\Delta^9$ THC, synthetic cannabinoid receptor agonists or anandamide degradation inhibitors (FAAH), or
  GABA analogues, such as gabapentin or pregabalin, or
  duloxetine, a serotonin and noradrenalin reuptake inhibitor.

In another embodiment, the pharmaceutical compositions comprise as active ingredient at least one of the compounds of the present invention in combination with methadone and at least one pharmaceutically acceptable excipient. In another embodiment, the present invention relates to a composition comprising:
  a) at least one compound of formula (1) as defined above, and
  b) at least one antinociceptive agent, for example selected from morphine and derivatives thereof, endocannabinoids, $\Delta^9$ THC, synthetic cannabinoid receptor agonists or anandamide degradation inhibitors (FAAH), or GABA analogues, such as gabapentin or pregabalin, or duloxetine, as combination product for simultaneous, separate or sequential use in the treatment of pain, in particular chronic or acute pain.

In the past, it has been shown that the combination of a mixed inhibitor having a chemical structure different from that of the compounds of the present invention with methadone made it possible to amplify synergistically the action of the constituents (Le Guen et al. (2003) *Pain,* 104, 139-148). This combination reduces the addictive processes of opiates and cocaine.

The pharmaceutical compositions according to the invention can be administered parenterally, such as intravenously or intradermally, or topically, orally or nasally. Forms that can be administered parenterally include aqueous suspensions, isotonic saline solutions or sterile injectable solutions which can contain pharmacologically compatible dispersants and/or wetting agents. Forms that can be administered orally include tablets, soft or hard capsules, powders, granules, oral solutions and suspensions. Forms that can be administered nasally include aerosols. Forms that can be administered topically include patches, gels, creams, ointments, lotions, sprays, collyria.

The effective dose of a compound of the invention varies as a function of numerous parameters such as, for example, the route of administration chosen and the weight, the age, the sex, the advancement of the pathology to be treated and the sensitivity of the individual to be treated. The present invention, according to another of its aspects, also relates to a method for treating the pathologies indicated above which comprises administration, to a patient in need thereof, of an effective dose of a compound according to the invention, or a pharmaceutically acceptable salt thereof or a composition according to the invention, preferably parenterally, orally or nasally.

Mixed NEP-APN inhibitors 1 can be prepared in two steps. In a first step, Boc beta-aminothiol 11 (Fournié-Zaluski M- C. et al. (1992) *J. Med. Chem.,* 35, 2473-2481) is activated by means of methoxycarbonylsulfonic acid chloride and then in a second phase is condensed with mercaptoalkanoic acids 10 to yield compounds 12.

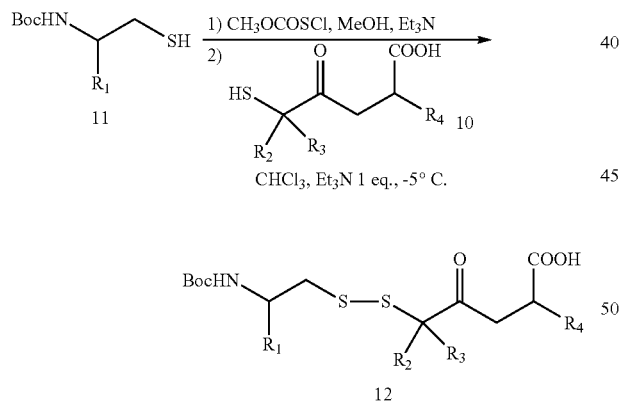

Esters 13 are obtained from acids 12 by reaction with the corresponding alcohol $R_5OH$ or by reflux in ethyl acetate with the chlorinated derivative $R_5Cl$ in the presence of $Et_3N$.

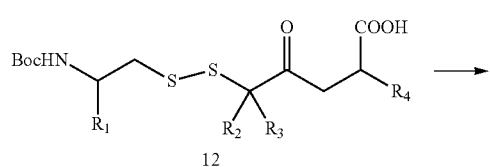

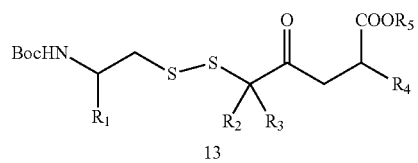

Deprotection of the N-terminal Boc group of 13 is carried out by action of formic acid, releasing 1.

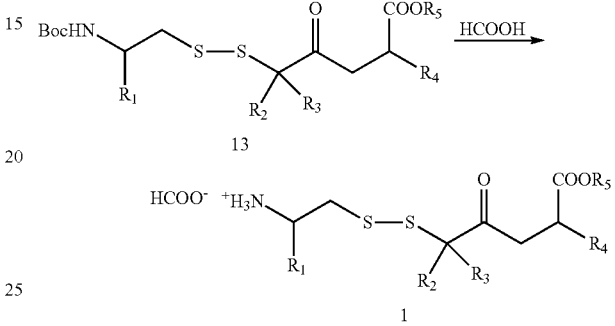

Alternatively, esters 1 can be obtained from 12, by deprotection of the N-terminal Boc group by action of formic acid followed by esterification by the corresponding alcohol in the presence of $SOCl_2$ at room temperature.

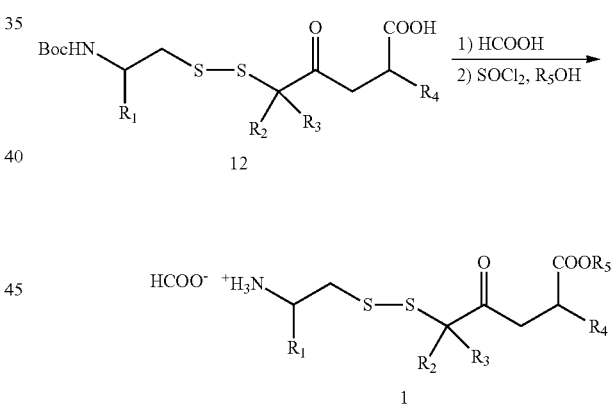

Alternatively, the N-protected compound 1 (R=iPrCOOCH($CH_3$)OCO) can be obtained from 12, by deprotection of the N-terminal Boc group by action of formic acid followed by condensation with 1-((2,5-dioxopyrrolidin-1-yloxy)carbonyloxy)ethyl isobutyrate in $CH_3CN$ in the presence of 2 N $NaHCO_3$ (Cundy et al. (2004) *J. Pharm. Exp. Therap.,* 311, 315-323).

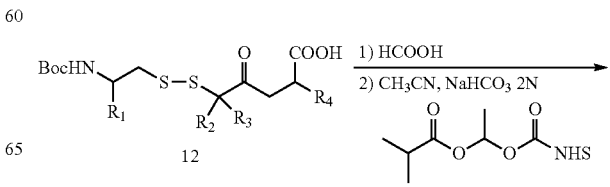

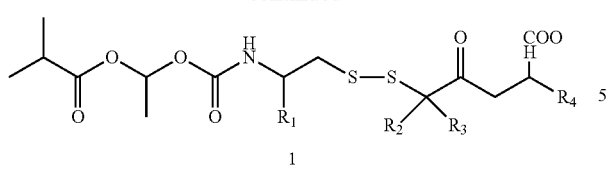

Compounds of formula 10 for which $R_3$=H and $R_5$=OH can be obtained in 5 steps from an amino acid 2 of defined absolute configuration, preferably (R).

Step 1:

Amino acid 2 is transformed into brominated derivative 3 by deamination-halogenation reaction, which, generally, is done with retention of configuration (Claeson G. et al. (1968) *Acta Chem. Scand.* 22, 3155-3159; Dutta A. et al. (1987) *J. Chem. Soc. Perkin Trans.* 1, 111-120).

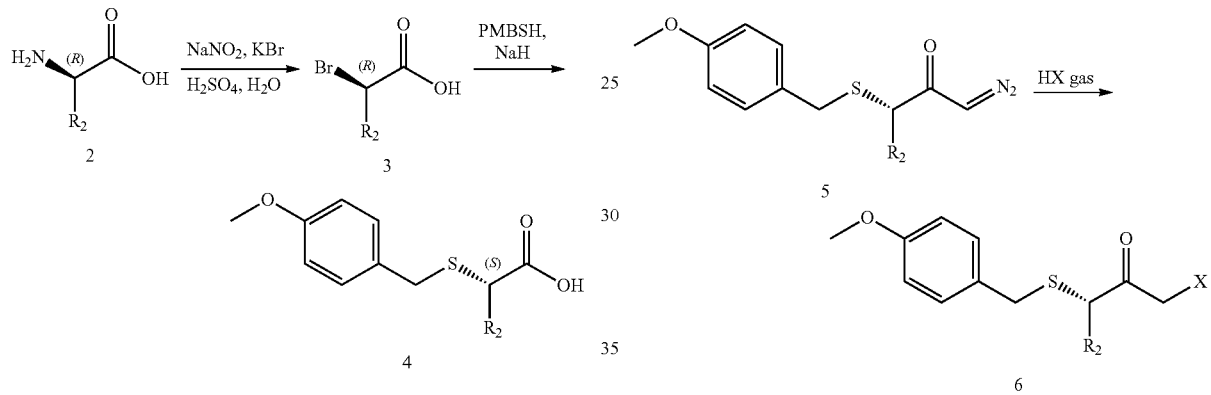

Brominated derivative 3 is transformed into thioether 4 by nucleophilic substitution with inversion of configuration by action of 4-methoxy-α-toluenethiol (PMBSH) in basic medium.

Step 2: Preparation of Halogenomethyl Ketone 6 from 4

Method 1: compound 4 is transformed into ketene 5 either from the mixed anhydride of 4 (prepared by action of isobutylchloroformate and N-methylmorpholine), or from the acid chloride (prepared by action of thionyl chloride on 4).

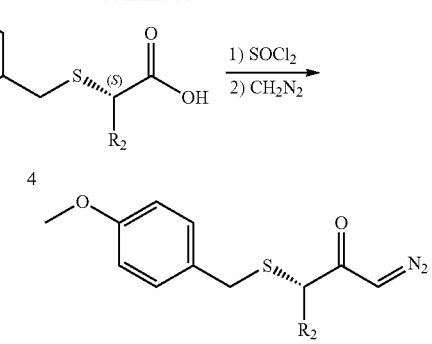

Ketene 5 is then transformed into halogenomethylketone 6 by bubbling of HCl gas or HBr gas in 1,4-dioxane, diethylether or ethyl acetate.

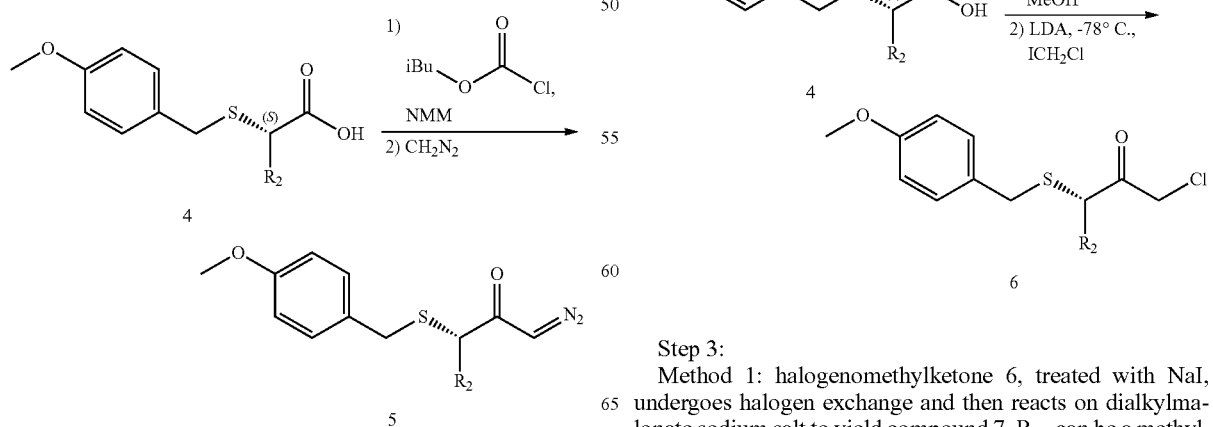

Method 2: alternatively, chloromethylketone 6 (X=Cl) can be obtained by action of chloroiodomyleane on the methyl ester of 4 (prepared in the presence of DMAP and EDCl or by action of acetyl chloride in methanol) in the presence of freshly prepared LDA (Chen et al. (1997) *Tet. Lett.* 38, 18, 3175-3178).

Step 3:

Method 1: halogenomethylketone 6, treated with NaI, undergoes halogen exchange and then reacts on dialkylmalonate sodium salt to yield compound 7. $R_{13}$ can be a methyl, ethyl or tert-butyl group.

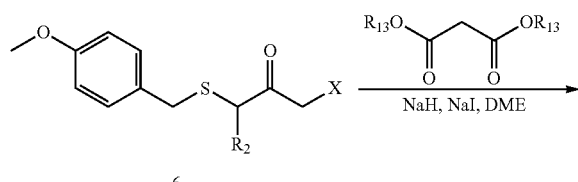
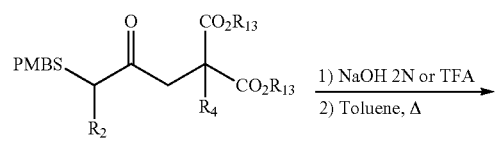
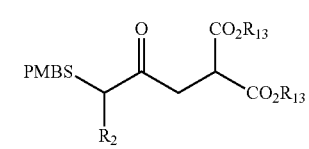

Substituent $R_4$ is introduced by action of brominated derivative $R_4Br$ on the anion of the preceding malonate 7, deprotonated in situ by NaH. Compound 8 is obtained.

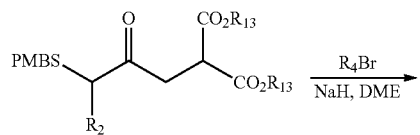

Method 2: substituent R4 can also be introduced directly on the halogenomethylketone 6, if X=Br. The latter, treated with NaI, undergoes halogen exchange and then reacts on the substituted dialkylmalonate sodium salt to yield compound 8.

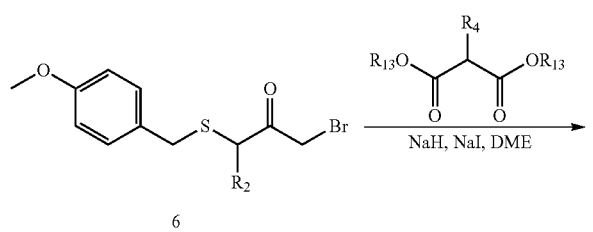

This reaction preserves the configuration of the carbon carrying the thiol.

Step 4:

After hydrolysis of the esters of 8, by action of TFA (when $R_{13}$ is a tert-butyl group) or by saponification (when $R_{13}$ is a methyl or ethyl group), decarboxylation with refluxing in toluene, for example, leads to compound 9.

Step 5:

Deprotection of the thiol present on compound 9 is carried out in 2 phases by action of DTNP (2,2'-dithiobis(5-nitropyridine)) in trifluoroacetic acid followed by reaction with TCEP (tris(2-carboxyethyl)phosphine) (Harris K. M. et al. (2007) *J. Pept. Sci.* (2), 81-93) or directly by heating in trifluoroacetic acid at 50° C. in the presence of anisole to yield mercaptoalkanoic acid 10.

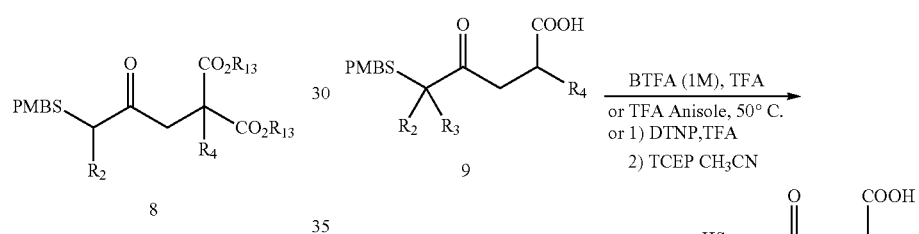

Compounds 10 in which $R_2=R_3=$alkyl, R=H and $R_5=$OH can be obtained by reaction between bromoacetic acid and 4-methoxy benzyl mercaptan to yield chloromethylketones 6, followed by double alkylation and transformation into chloromethylketone 6 as described above.

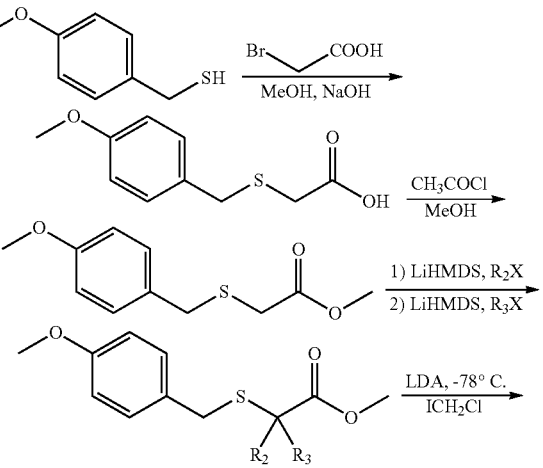

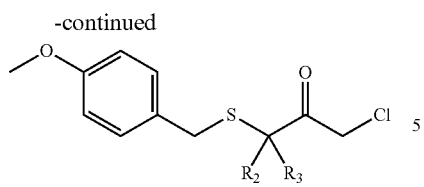

Compounds 10 in which $R_2$ and $R_3$ form a ring can be obtained by preparation of chloromethylketone 6 directly from the corresponding ester (methyl, for example) by alkylation using 4-methoxy benzyl mercaptan disulfide (or from another activation of this thiol) and transformation into chloromethylketone 6.

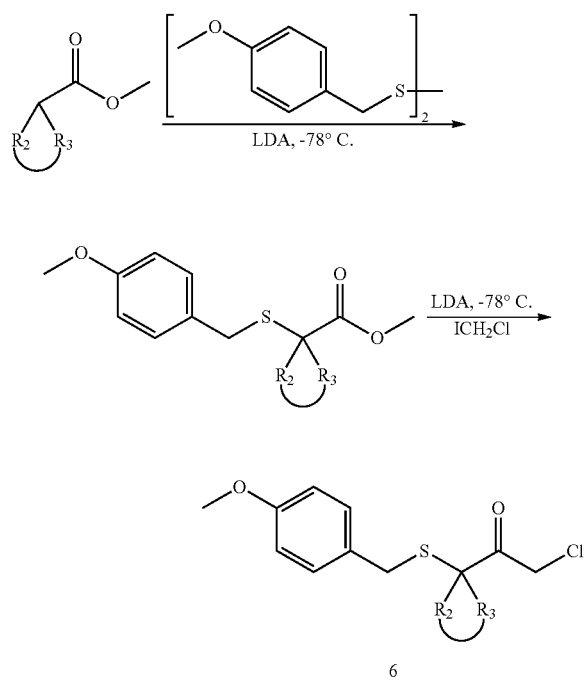

Alternatively, the cyclic geminate chloromethylketone 6 can be prepared directly from the corresponding ester (methyl, for example) by alkylation using activated 4-methoxy benzyl mercaptan and transformation into bromomethylketone 6 using $TMSN_2$ solution.

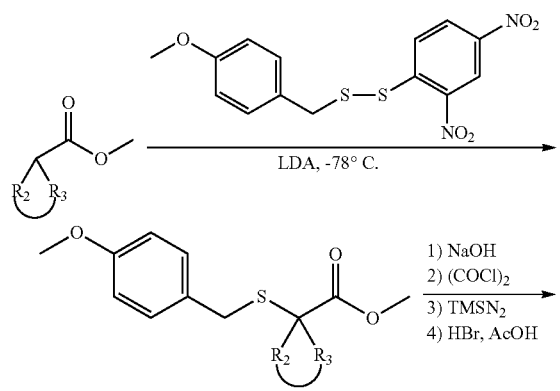

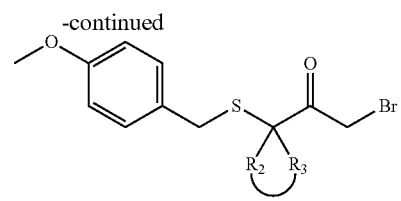

The rest of the synthesis is carried out as described above.

When $R_4$ is 4-bromobenzyl, compound 9 can undergo a Suzuki reaction to introduce an aromatic on the benzyl.

Compounds 9, when $R_3$=H, have 2 centers of asymmetry and are comprised of 4 stereoisomers. When $R_2$=$R_3$=alkyl or ring, compounds 9 have only one center of asymmetry and are thus a mixture of 2 stereoisomers. Compounds 10 are obtained after deprotection of 9. If compounds 9 are chiral, they can be separated by selective precipitation with chiral amines such as α-methylbenzylamine or norephedrine or by chiral column HPLC.

EXAMPLES

The invention will be further illustrated without in any way being limited by the examples below.

1. Synthesis of Mixed NEP-APN Inhibitors
1.1 Synthesis of NEP Inhibitors
1.1.1 Step 1: Synthesis of (R)-2-Bromo Carboxylic Acids

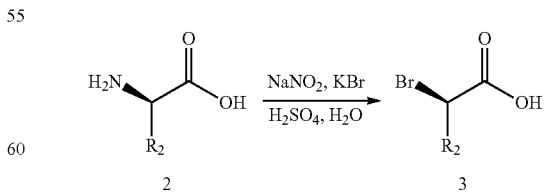

The amino acid of configuration (R)— (39.3 mmol) is solubilized in 50 ml of water. At 0° C., KBr (3.5 eq, 31.8 g) and then $H_2SO_4$ (7.73 ml), respectively, are added dropwise, while maintaining the temperature below 5° C. The mixture is cooled to −10° C. and NaNO₂ (1.3 eq, 3.59 g) solubilized in 17 ml of water is added dropwise. The mixture is stirred for 2 hours at −5° C.

After returning to room temperature, the mixture is extracted with CH₂Cl₂ (2×50 ml). The organic phase is washed with H₂O, saturated NaCl, dried on Na₂SO₄ to yield the expected product of configuration (R).

3a R₂=CH₂Ph: light yellow oil; (Yield: 50%); Rf (CH₂Cl₂/MeOH): 0.62

NMR (CDCl₃, 200 MHz): 3.15-3.40 (2H, dd); 4.69 (1H, m); 7.20-7.40 (5H, m)

3b R₂=CH₂CH(CH₃)₂: Oil; (Yield: 82.5%); Rf (CH₂Cl₂/MeOH): 0.49

NMR (CDCl₃, 200 MHz): 0.90-1.0 (6H, m); 1.55 (2H, m); 2.40 (1H, m); 4.29 (1H, d)

3c R₂=CH₂(4-Br-Ph): light yellow oil; (Yield: 50%); Rf (CH₂Cl₂/MeOH): 0.62

NMR (CDCl₃, 200 MHz): 3.15-3.40 (2H, dd); 4.70 (1H, m); 7.20-7.40 (4H, m)

3d R₂=CH₂(4-Ph-Ph): light yellow oil; (Yield: 60%); Rf (CH₂Cl₂/MeOH): 0.7

NMR (CDCl₃, 200 MHz): 3.15-3.40 (2H, dd); 4.70 (1H, m); 7.20-7.60 (9H, m)

Synthesis of (S)-2-(4-methoxybenzylthio) Carboxylic Acids

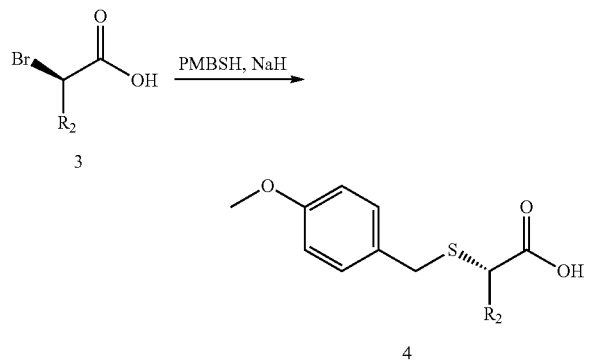

Under inert atmosphere, 4-methoxybenzyl mercaptan (4.2 ml; 30.06 mmol, 1 eq) is solubilized in 70 ml of anhydrous THF and 1.1 eq of 60% NaH (1.33 g; 33.07 mmol) is added. The mixture is stirred for 15 minutes at room temperature and then the brominated derivative 3 (1 eq, 30.06 mmol) solubilized in 30 ml of THF is added to bromine dropwise using a dropper. The mixture is stirred overnight at room temperature. The mixture is evaporated dry and then is taken up in AcOEt.

The organic phase is washed with H₂O, saturated NaCl, dried with Na₂SO₄, evaporated under reduced pressure to yield the crude product. The latter is purified by chromatography on silica with CHex/AcOEt 5/5 as elution system to yield compound 4 of configuration (S) in the form of oil.

4a R₂=CH₂Ph: oil; (Yield: 40%); Rf (CH₂Cl₂/MeOH/9/1): 0.5

NMR (CDCl₃, 200 MHz): 2.80-3.10 (2H, m); 3.68 (2H, s); 3.76 (3H, s); 4.53 (1H, t); 6.84 (2H, d); 7.09-7.49 (7H, m)

4b R₂=CH₂CH(CH₃)₂: Oil; (Yield: 26%); Rf (CHex/AcOEt): 0.65

NMR (CDCl₃, 200 MHz): 0.90-1.0 (6H, m); 1.55 (2H, m); 2.25 (1H, m); 3.40 (1H, d); 3.70 (2H, s); 3.90 (3H, s); 6.8-6.9 (4H, m)

4c R₂=CH₂(4-Br-Ph): oil; (Yield: 40%); Rf (CH₂Cl₂/MeOH/9/1): 0.5

NMR (CDCl₃, 200 MHz): 3.0-3.30 (2H, m); 3.60 (1H, q); 3.70 (2H, s); 3.90 (3H, s); 6.80-7.20 (8H, m)

4d R₂=CH₂(4-Ph-Ph): oil; (Yield: 50%); Rf (CH₂Cl₂/MeOH/9/1): 0.6

NMR (CDCl₃, 200 MHz): 3.0-3.30 (2H, m); 3.60 (1H, q); 3.70 (2H, s); 3.90 (3H, s); 6.80-7.2 (13H, m)

1.1.2 Step 2:
Procedure 1:
Method 1: Synthesis of Diazoketone from Mixed Anhydride

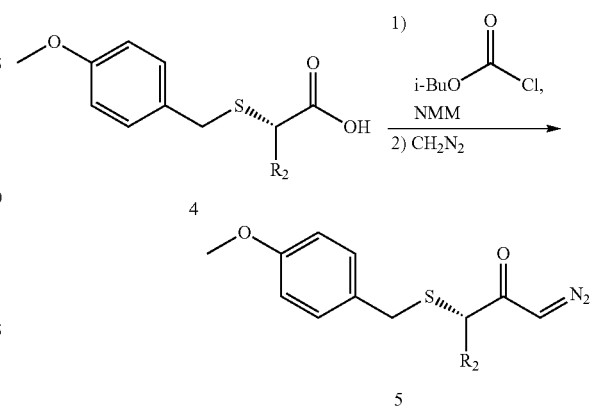

To a solution of acid 4 (18.5 mmol) in 20 ml of dry THF, under inert atmosphere at −20° C., N-methyl morpholine (2.15 ml; 1.05 eq) and iBuOCOCl (2.52 ml; 1.05 eq) are added successively. The mixture is stirred for 5-10 minutes at −20° C. and then the precipitate is filtered on Celite and washed with 20 ml of THF.

The solution of CH₂N2 in ether (2.5 eq) (prepared beforehand from Diazald® and KOH in carbitol), is transferred to the activated ester solution at 0° C. The solution becomes yellow. The mixture is stirred for 2 hours at room temperature.

Method 2: Synthesis of Diazoketone from Acid Chloride

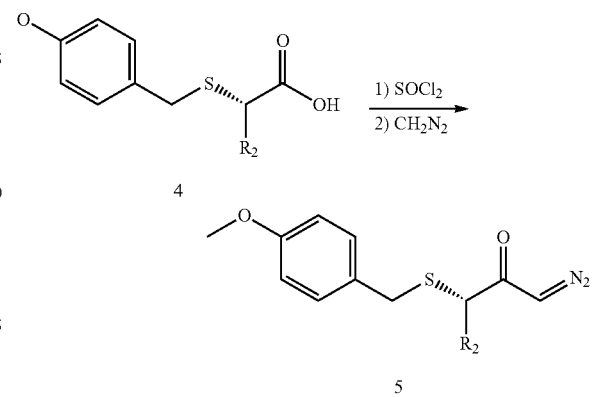

Acid 4 (14.5 mmol) is solubilized in 23 ml of anhydrous CH₂Cl₂. SOCl₂ (1.5 eq; 21.75 mmol) is added at room temperature and the mixture is refluxed for 2 hours under inert atmosphere. The mixture is then evaporated dry to yield a brown oil. The product is solubilized in anhydrous THF at a concentration of 5 mmol/ml.

The solution of CH₂N2 (2.5 eq) in ether, prepared beforehand, is transferred to the acid chloride solution at 0° C. The solution becomes yellow. The mixture is stirred for 2 hours at room temperature, under inert atmosphere.

Synthesis of Chloromethylketone

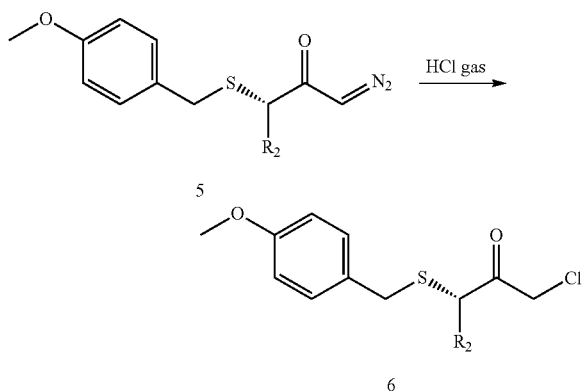

The solution of compound 5 is placed, under inert atmosphere, in a three-necked flask maintained at 0° C. The mixture is saturated with HCl, by bubbling at 0° C. After 30 min, the solvent and the excess HCl are evaporated under reduced pressure. The product is taken up in AcOEt (150 ml) and then is washed with 10% NaHCO$_3$, H$_2$O and dried on Na$_2$SO$_4$ to yield the product in the crude state. The latter is used as-is without purification for the following step.

Procedure 2: Synthesis from the Methyl Ester

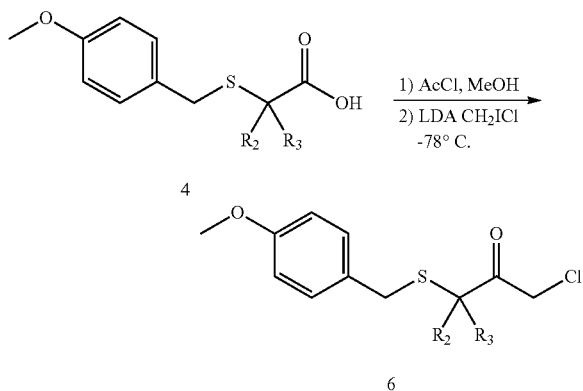

Acetyl chloride (3 eq; 2 ml) is added dropwise at 0° C., under inert gas, to an acid solution 4 (9.1 mmol) in 50 ml of anhydrous MeOH. The mixture is stirred overnight at room temperature. The mixture is concentrated under reduced pressure, taken up in MTBE (methyl-tert-butyl ether) (200 ml). The organic phase is washed with 10% NaHCO$_3$ (100 ml), H$_2$O (100 ml) and saturated NaCl (100 ml). The organic phase is dried on Na$_2$SO$_4$ and then concentrated under reduced pressure to yield methyl ester in the crude state. The latter is purified by flash chromatography on silica gel.

A solution of LDA (5 eq) in THF (55 ml), freshly prepared from 1.6 M BuLi in hexane (15 ml) and diisopropylamine (3.4 ml), is added dropwise over 30 min to the methyl ester (4.42 mmol) and chloroiodomethane (1.3 ml; 4 eq) in solution in 25 ml of THF. The internal temperature of the reaction is maintained below −70° C. during the addition and at −75° C. for 10 minutes. Acetic acid solution (6 ml in 44 ml of THF) is added while keeping the temperature below −65° C., to neutralize the medium. The mixture is then extracted with AcOEt. The organic phase is washed with 10% NaHCO$_3$, 10% citric acid, saturated NaCl, dried on Na$_2$SO$_4$, then concentrated under reduced pressure to yield the crude product which is used as-is for the following step.

6a R$_2$=CH$_2$Ph; R$_3$=H: orange oil; (Yield: 93.0%); Rf (CHex/AcOEt 6/4): 0.73

HPLC: Kromasil C18 CH$_3$CN(0.1% TFA)/H$_2$O (0.1% TFA) 60/40 Rt: 19.18 min

NMR (CDCl$_3$, 200 MHz): 2.85 (1H, dd); 3.2 (1H, dd); 3.55 (1H, d); 3.6 (2H, d); 3.7 (3H, s); 4.1 (2H, d); 6.7 (2H, d); 7.2-7.4 (7H, m)

6b R$_2$=CH$_2$CH(CH$_3$)$_2$; R$_3$=H: oil orange; (Yield: 94.0%); Rf (CHex/AcOEt 5/5): 0.68

NMR (CDCl$_3$, 200 MHz): 0.90-1.0 (6H, m); 1.55 (2H, m); 2.25 (1H, m); 3.40 (1H, d); 3.70 (2H, s); 3.90 (3H, s); 4.25 (2H, d); 6.80 (2H, d); 7.15 (2H, d)

6c R$_2$=CH$_2$(4-Br-Ph); R$_3$=H: orange oil; (Yield: 85.0%); Rf (CHex/AcOEt 6/4): 0.80

NMR (CDCl$_3$, 200 MHz): 2.85 (1H, dd); 3.2 (1H, dd); 3.55 (1H, d); 3.6 (2H, d); 3.7 (3H, s); 4.1 (2H, s); 6.7 (2H, d); 7.2-7.4 (6H, m)

6d R$_2$=CH$_2$(4-Ph-Ph); R$_3$=H: orange oil; (Yield: 90.0%); Rf (CHex/AcOEt 6/4): 0.73

NMR (CDCl$_3$, 200 MHz): 2.85 (1H, dd); 3.2 (1H, dd); 3.55 (1H, d); 3.6 (2H, d); 3.7 (3H, s); 4.1 (2H, d); 6.7 (2H, d); 7.2-7.5 (11H, m)

Synthesis of Geminate Chloromethylketones

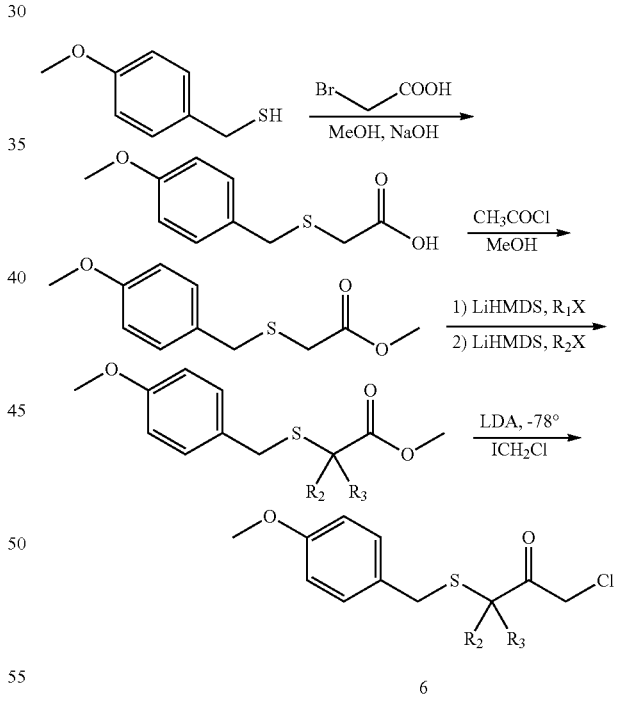

Bromoacetic acid (10 g, 72 mmol) is dissolved, under inert atmosphere, in 50 ml of MeOH. 11 ml (1.1 eq) of 4-methoxybenzyl mercaptan is added at 4° C. and alcoholic sodium hydroxide solution (6.4 g of NaOH (2.2 eq) in solution in 100 ml of MeOH) is added dropwise. The mixture is stirred for 40 minutes at room temperature. The solvent is evaporated under reduced pressure. The product is taken up in Et$_2$O (200 ml) and 350 ml of 10% NaHCO$_3$. The aqueous phase is acidified to pH=1 and then extracted with 350 ml of Et$_2$O. The organic phase is washed with H$_2$O (100 ml), saturated NaCl (100 ml)

and dried on Na$_2$SO$_4$ to yield 15 g of a crude white solid (yield: 98%) which is used as-is for the following step.

HPLC: Atlantis T3, CH$_3$CN(0.1% TFA)/H$_2$O (0.1% TFA) Gradient 10-90% 15 min, Rt=10.64 min NMR (CDCl$_3$, 200 MHz): 3.0 (2H, s); 3.75 (3H, s); 3.75 (2H, s); 6.80 (2H, d); 7.20 (2H, d)

Acetyl chloride (1.5 eq; 7.6 ml; 106 mmol) is added dropwise at 4° C., under inert atmosphere, to a solution of the preceding acid (70.8 mmol) in 150 ml of anhydrous MeOH. The mixture is stirred overnight at room temperature. The mixture is concentrated under reduced pressure, taken up in MTBE (methyl-tert-butyl ether) (350 ml). The organic phase is washed with 0.5 N HCl (2×100 ml), 10% NaHCO$_3$ (2×100 ml), H$_2$O (100 ml) and saturated NaCl (100 ml). The organic phase is dried on Na$_2$SO$_4$ and then concentrated under reduced pressure to yield the methyl ester.

HPLC: Atlantis T3, CH$_3$CN(0.1% TFA)/H$_2$O (0.1% TFA) Gradient 50-90% 10 min, Rt=5.24 min NMR (CDCl$_3$, 200 MHz): 3.1 (2H, s); 3.75 (3H, s); 3.83 (2H, s); 3.85 (3H, s); 6.85 (2H, d); 7.30 (2H, d).

A solution of 1 M LiHMDS in THF (4.4 ml; 1 eq) is added dropwise, under inert atmosphere, at −78° C., to a solution of the preceding ester (1 g; 4.4 mmol; 1 eq) solubilized in 5 ml of anhydrous THF. The mixture is stirred for 1 hour at −78° C. and then the solution of the derivative RX (1 eq) is added under inert atmosphere at −78° C. The mixture, returned to room temperature, is stirred for 3 hours. The mixture is again cooled to −78° C. and 1 eq of LiHMDS is added followed by 1.5 eq of RX. The mixture, returned to room temperature, is stirred for 4 hours. The mixture is then partitioned between 200 ml of 1 N HCl and 300 ml of AcOEt. The organic phase is dried on Na$_2$SO$_4$ and then concentrated under reduced pressure to yield the crude product which purified by chromatography on silica gel.

R$_2$=CH$_3$, R$_3$=CH$_3$: Oil (Yield: 44%)

HPLC: Atlantis T3, CH$_3$CN(0.1% TFA)/H$_2$O (0.1% TFA) Gradient 50-90% 10 min, Rt=7.39 min NMR (CDCl$_3$, 200 MHz): 1.60 (6H, s); 3.70 (3H, s); 3.80 (2H, s); 3.80 (3H, s); 6.85 (2H, d); 7.25 (2H, d)

R$_2$=C$_2$H$_5$, R$_3$=C$_2$H$_5$: oil (Yield: 55%)

HPLC: Atlantis T3, CH$_3$CN(0.1% TFA)/H$_2$O (0.1% TFA) Gradient 50-90% 10 min, Rt=9.72 min NMR (CDCl$_3$, 200 MHz): 0.90 (6H, t); 1.85 (4H, m); 3.68 (2H, s); 3.70 (3H, s); 3.80 (3H, s); 6.82 (2H, d); 7.22 (2H, d)

The chloromethylketone is synthesized as described in 4b.

6e R$_2$=CH$_3$, R$_3$=CH$_3$: amber oil

HPLC: Atlantis T3, CH$_3$CN(0.1% TFA)/H$_2$O (0.1% TFA) Gradient 50-90% 10 min, Rt=7.91 min NMR (CDCl$_3$, 200 MHz): 1.60 (6H, s); 3.55 (1H, d); 3.60 (2H, s); 3.80 (3H, s); 4.45 (2H, s); 6.7 (2H, d); 7.2 (2H, d)

6f R$_2$=C$_2$H$_5$, R$_3$=C$_2$H$_5$: amber oil

HPLC: Atlantis T3, CH$_3$CN(0.1% TFA)/H$_2$O (0.1% TFA) Gradient 50-90% 10 min, Rt=10.04 min NMR (CDCl$_3$, 200 MHz): 0.85 (6H, t); 1.80 (4H, q); 3.55 (1H, d); 3.60 (2H, s); 3.80 (3H, s); 4.45 (2H, s); 6.7 (2H, d); 7.2 (2H, d)

Synthesis of Cyclic Chloromethylketones
Method 1:

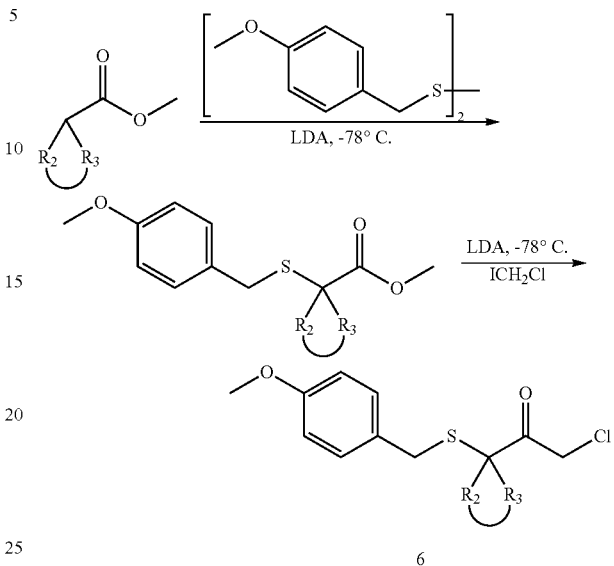

A 2.5 M solution of BuLi in hexane (2.77 mmol; 1.1 ml; 1.2 eq) is added at −10° C. to a solution of DIPA (diisopropylethylamine) (3 mmol; 1.3 eq; 420 µl) in THF (9 ml) under inert atmosphere. The mixture is stirred for 1 hour at 0° C. This LDA solution, freshly prepared, is added dropwise to a solution of cyclopentanoic acid methyl ester in 5 ml of THF at −55° C. The mixture is stirred for 1 hour at −55° C. under inert atmosphere. HMPA (hexylmethylphophoramide) (3.46 mmol; 1.5 eq; 610 µl) is added and the mixture is stirred for 10 minutes at the same temperature. A solution of 4-methoxybenzyl mercaptan disulfide (3 mmol; 1.3 eq; 920 mg) in 12 ml of THF is then added dropwise at −55° C. After returning to room temperature, the mixture is stirred overnight. The mixture is partitioned between 10 ml of saturated NH$_4$Cl and 20 ml of AcOEt. The organic phase is washed with saturated NH$_4$Cl (2×10 ml), saturated NaCl (2×15 ml), dried on Na$_2$SO$_4$ and then concentrated under reduced pressure to yield the crude product which is purified by chromatography on silica gel.

C(R$_2$R$_3$)=Cyclopentyl: oil (Yield: 40%)

HPLC: Atlantis T3, CH$_3$CN(0.1% TFA)/H$_2$O (0.1% TFA) Gradient 30-90% 10 min, Rt=9.68 min NMR (CDCl$_3$, 200 MHz): 1.60-2.40 (8H, m); 3.67 (3H, s); 3.77 (2H, s); 3.80 (3H, s); 6.83 (2H, d); 7.24 (2H, d)

The chloromethylketone is synthesized as described in 4b.

6g C(R$_2$)(R$_3$)=Cyclopentyl: amber oil

HPLC: Atlantis T3, CH$_3$CN(0.1% TFA)/H$_2$O (0.1% TFA) Gradient 60-90% 10 min, Rt=6.47 min NMR (CDCl$_3$, 200 MHz): 1.60-1.80 (8H, m); 3.54 (2H, s); 3.80 (3H, s); 4.47 (2H, s); 6.78 (2H, d); 7.22 (2H, d)

6h C(R$_2$)(R$_3$)=Cyclohexyl: amber oil

HPLC: Atlantis T3, CH$_3$CN(0.1% TFA)/H$_2$O (0.1% TFA) Gradient 70-90% 10 min, Rt=8.11 min NMR (CDCl$_3$, 200 MHz): 1.40-2.20 (10H, m); 3.45 (2H, s); 3.80 (3H, s); 4.40 (2H, s); 6.80 (2H, d); 7.20 (2H, d)

Method 2:

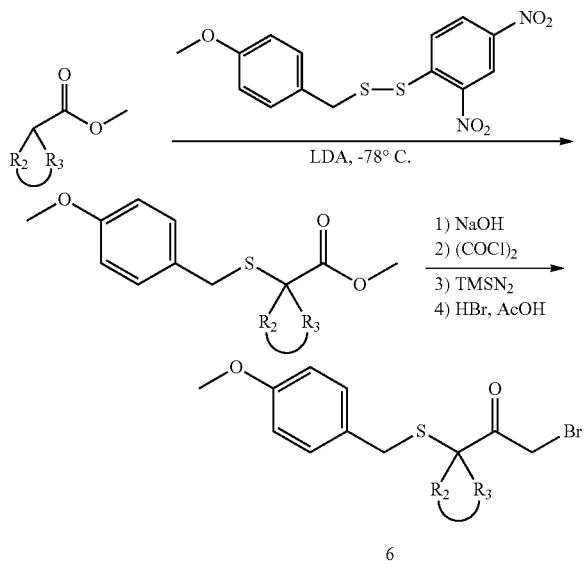

A 2.5 M solution of BuLi in hexane (16 mmol; 6.4 ml; 1.15 eq) is added at −10° C. to a solution of DIPA (diisopropylethylamine) (16.7 mmol; 1.2 eq; 2.34 ml) in THF (10 ml) under inert atmosphere. The mixture is stirred for 1 hour at 0° C. This LDA solution, freshly prepared, is added dropwise to a solution of phenylcyclopentanoic acid methyl ester in 5 ml of THF and HMPA (hexylmethylphophoramide) (1.0 eq; 2.5 ml) at −78° C. The mixture is stirred for 1 hour at −78° C. under inert atmosphere. Activated 4-methoxybenzyl mercaptan thiol (18 mmol; 1.3 eq; 6.37 mg) is added in the solid state at −78° C. The mixture is stirred for 1.5 hours at −78° C. The mixture is partitioned between 200 ml of 1 N HCl and 200 ml of AcOEt. The organic phase is diluted with 200 ml of AcOEt, washed with saturated NaCl (200 ml), dried on $Na_2SO_4$ and then concentrated under reduced pressure to yield the crude product which is purified by chromatography on silica gel.

$C(R_2R_3)$=PhenylCyclopentyl (Indanyl): white solid (Yield: 25%)

HPLC: Atlantis T3, $CH_3CN$(0.1% TFA)/$H_2O$ (0.1% TFA) Gradient 50-90% 10 min, Rt=9.59 min NMR ($CDCl_3$, 200 MHz): 2.90-3.70 (6H, m); 3.55 (3H, s); 3.65 (3H, s); 6.60-7.10 (8H, m)

The product of the preceding step (1.13 g; 3.44 mmol) is solubilized in 14 ml of THF/MeOH mixture. 14 ml of 2 N NaOH is added and the mixture is stirred for 3 hours at room temperature. The mixture is diluted with 40 ml of $H_2O$. The mixture is concentrated under reduced pressure. The aqueous phase is acidified with 1 N HCl and then extracted with MTBE (3×100 ml), washed with saturated NaCl (100 ml), dried on $Na_2SO_4$ and then concentrated under reduced pressure to yield a white solid (Yield: 98%).

HPLC: Atlantis T3, $CH_3CN$(0.1% TFA)/$H_2O$ (0.1% TFA) Gradient 50-90% 10 min, Rt=6.50 min Oxalyl chloride (2 mmol; 1.5 eq; 177 μl) is added dropwise, under inert atmosphere, at 0° C., to a solution of the preceding acid (1.38 mmol; 434 mg) in 10 ml of $CH_2Cl_2$, in the presence of 20 μl of DMF (0.2 eq). The mixture is allowed to return to room temperature and then is stirred for 30 minutes at room temperature.

HPLC: Atlantis T3, $CH_3CN$(0.1% TFA)/$H_2O$ (0.1% TFA) Gradient 70-90% 10 min, Rt=6.70 min.

After evaporation under reduced pressure, the acid chloride is taken up, under inert atmosphere, in anhydrous $CH_3CN$ (5 ml) and $TMSCHN_2$ (1 M in $Et_2O$) (1.5 eq; 1 ml) is added dropwise at 0° C. The mixture is allowed to return to room temperature and then is stirred for 1.5 hours. The mixture is then trapped by 300 μl (1.65 mmol; 1.2 eq) of 33% HBr in acetic acid. The mixture is stirred for 15 minutes at room temperature. The mixture is concentrated under reduced pressure and then taken up in MTBE (200 ml). The organic phase is washed with 10% $NaHCO_3$ (100 ml), saturated NaCl (50 ml), dried on $Na_2SO_4$ and then concentrated under reduced pressure to yield compound 6h in the form of a brown oil (Yield: 83%).

6h $C(R_2R_3)$=Phenylcyclopentyl (Indanyl): white solid

HPLC: Atlantis T3, $CH_3CN$(0.1% TFA)/$H_2O$ (0.1% TFA) Gradient 70-90% 10 min, Rt=5.30 min NMR ($CDCl_3$, 200 MHz): 2.90-3.70 (6H, m); 3.65 (3H, s); 4.15 (2H, s); 6.60-7.10 (8H, m)

1.1.3 Step 3
Method 1:

Under inert atmosphere, 980 mg of 60% NaH (1 eq) is added to dialkylmalonate (1 eq) in 25 ml (1 ml/mmol) of DME (1,2-dimethoxyethane). The mixture is stirred for 1 hour at room temperature.

A mixture of chloromethylketone 6 (24.42 mmol) and NaI (24.42 mmol, 3.66 g, 1 eq) in 50 ml of DME is stirred at room temperature for 15 minutes and then added to freshly prepared dialkylmalonate sodium salt solution. The mixture is stirred for 4 hours at room temperature.

At the end of the reaction, the solvent is evaporated under reduced pressure. The product is taken up in dichloromethane. The organic phase is washed with water and dried on $Na_2SO_4$. The product is purified by chromatography on silica column with CHex/AcOEt 9/1 as elution system.

7a1 $R_2$=$CH_2Ph$, $R_3$=H, $R_{13}$=$CH_2CH_3$: orange oil; (Yield: 60%); Rf (CHex/AcOEt 9/1): 0.16

HPLC: Kromasil C18 $CH_3CN$/$H_2O$ (0.1% TFA) 80/20 Rt: 6.57 min

NMR ($CDCl_3$, 200 MHz): 1.30 (6H, t); 2.70-3.40 (4H, m); 3.45 (1H, t); 3.50 (2H, d); 3.60 (1H, t); 3.65 (3H, s); 4.15 (4H, q); 6.75 (2H, d); 7.2-7.4 (7H, m)

7a2 $R_2$=$CH_2Ph$, $R_3$=H, $R_{13}$=tBu: orange oil; (Yield: 62%); Rf (CHex/AcOEt 9/1): 0.36

HPLC: Kromasil C18 $CH_3CN$/$H_2O$ (0.1% TFA) 85/15 Rt: 15.51 min

NMR ($CDCl_3$, 200 MHz): 1.40 (18H, s); 2.70-3.40 (4H, m); 3.45 (1H, t); 3.50 (2H, d); 3.60 (1H, t); 3.65 (3H, s); 6.75 (2H, d); 7.2-7.4 (7H, m)

7b $R_2$=$CH_2CH(CH_3)_2$, $R_3$=H, $R_{13}$=tBu: orange oil; (Yield: 30%); Rf (CHex/AcOEt 9/1): 0.49

HPLC: Kromasil C18 CH$_3$CN/H$_2$O (0.1% TFA) 90/10 Rt: 6.49 min

NMR (CDCl$_3$, 200 MHz): 0.90-1.0 (6H, m), 1.40 (18H, s); 1.55 (2H, m); 2.15 (1H, m); 3.19 (2H, m); 3.40 (2H, m); 3.50 (2H, d); 3.80 (3H, s); 6.75 (2H, d); 7.2 (2H, d)

7c R$_2$=CH$_2$(4-Br-Ph), R$_3$=H, R$_{13}$=tBu: orange oil; (Yield: 62%); Rf (CHex/AcOEt 9/1): 0.36

HPLC: Kromasil C18 CH$_3$CN/H$_2$O (0.1% TFA) 85/15 Rt: 15.51 min

NMR (CDCl$_3$, 200 MHz): 1.40 (18H, s); 2.70-3.40 (4H, m); 3.45 (1H, t); 3.50 (2H, d); 3.60 (1H, t); 3.65 (3H, s); 6.75 (2H, d); 7.2-7.4 (6H, m)

7d R$_2$=CH$_2$(4-Ph-Ph), R$_3$=H, R$_{13}$=tBu: orange oil; (Yield: 60%); Rf (CHex/AcOEt 9/1): 0.36

HPLC: Kromasil C18 CH$_3$CN/H$_2$O (0.1% TFA) 85/15 Rt: 16.71 min

NMR (CDCl$_3$, 200 MHz): 1.40 (18H, s); 2.70-3.40 (4H, m); 3.45 (1H, t); 3.50 (2H, d); 3.60 (1H, t); 3.65 (3H, s); 6.75 (2H, d); 7.2-7.5 (11H, m)

7e R$_2$=CH$_3$, R$_3$=CH$_3$, R$_{13}$=Et (Yield: 40%)

HPLC: Atlantis T3, CH$_3$CN(0.1% TFA)/H$_2$O (0.1% TFA) Gradient 70-90% 10 min, Rt=4.87 min NMR (CDCl$_3$, 200 MHz): 1.30 (6H, t); 1.55 (6H, s); 3.40 (2H, d); 3.55 (2H, s); 3.75 (1H, t); 3.82 (3H, s); 4.25 (4H, q); 6.85 (2H, d); 7.25 (2H, d)

7f R$_2$=C$_2$H$_5$, R$_3$=C$_2$H$_5$, R$_{13}$=Et (Yield: 30%)

HPLC: Atlantis T3, CH$_3$CN(0.1% TFA)/H$_2$O (0.1% TFA) Gradient 50-90% 10 min then 90-50%, Rt=11.56 min NMR (CDCl$_3$, 200 MHz): 0.80 (6H, t); 1.20 (6H, t); 1.75 (4H, m); 3.30 (2H, s); 3.38 (2H, d); 3.65 (1H, t); 3.72 (3H, s); 4.15 (4H, q); 6.72 (2H, d); 7.15 (2H, d)

7g C(R$_2$)(R$_3$)=Cyclopentyl, R$_{13}$: Et (Yield: 24%)

HPLC: Atlantis T3, CH$_3$CN(0.1% TFA)/H$_2$O (0.1% TFA) Gradient 60-90% 10 min, Rt=8.04 min NMR (CDCl$_3$, 200 MHz): 1.29 (6H, t); 1.60-2.30 (8H, m); 3.39 (2H, d); 3.52 (2H, s); 3.74 (1H, t); 3.79 (3H, s); 4.22 (4H, q); 6.83 (2H, d); 7.20 (2H, d)

7h C(R$_2$)(R$_3$)=Cyclohexyl, R$_{13}$: Et (Yield: 33%)

HPLC: Atlantis T3, CH$_3$CN(0.1% TFA)/H$_2$O (0.1% TFA) Gradient 70-90% 10 min, Rt=7.76 min NMR (CDCl$_3$, 200 MHz): 1.29 (6H, t); 1.60-2.30 (10H, m); 3.45 (2H, d); 3.50 (2H, s); 3.75 (1H, t); 3.80 (3H, s); 4.25 (4H, q); 6.85 (2H, d); 7.20 (2H, d)

7i C(R$_2$)(R$_3$)=Phenylcyclopentyl (Indanyl), R$_{13}$: Et (Yield: 80%)

HPLC: Atlantis T3, CH$_3$CN(0.1% TFA)/H$_2$O (0.1% TFA) Gradient 70-90% 10 min, Rt=6.57 min NMR (CDCl$_3$, 200 MHz): 1.20 (6H, t); 2.90-3.60 (9H, m); 3.65 (3H, s); 4.15 (4H, q); 6.60-7.10 (8H, m)

Alkylation of the Malonate

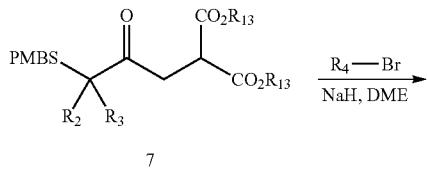

To a solution of product 7 in 15 ml of DME (dimethoxyethane), 1.5 eq of 60% NaH is added.

The mixture is stirred for 1 hour at room temperature and then the brominated derivative R$_4$Br (3 eq) is added. The mixture is stirred overnight at room temperature.

The solvent is evaporated under reduced pressure and then the mixture is taken up in H$_2$O and AcOEt. The organic phase is washed with H$_2$O, dried on Na$_2$SO$_4$ and then concentrated under reduced pressure. The product is purified by chromatography on silica with CHex/AcOEt 9/1 as elution system to yield the desired product 8.

8a R$_2$=CH$_2$Ph; R$_3$=H; R$_4$=CH$_2$(4-Br-Ph); R$_{13}$=Et: orange oil

8b R$_2$=CH$_2$Ph; R$_3$=H; R$_4$=CH$_2$Ph; R$_{13}$=tBu: orange oil

8c R$_2$=CH$_2$CH(CH$_3$)$_2$; R$_3$=H; R$_4$=CH$_2$(4-Ph-Ph); R$_{13}$=Et: orange oil 8d R$_2$=CH$_2$CH(CH$_3$)$_2$; R$_3$=H; R$_4$=CH$_2$Ph; R$_{13}$=Et: orange oil 8e R$_2$=CH$_2$CH(CH$_3$)$_2$; R$_3$=H; R$_4$=CH$_2$(4-Br-Ph); R$_{13}$=Et: orange oil 8f R$_2$=CH$_2$(4-Br-Ph); R$_3$=H; R$_4$=CH$_2$Ph; R$_{13}$=tBu: orange oil 8g R$_2$=CH$_2$(4-Br-Ph); R$_3$=H; R$_4$=CH$_2$(4-Br-Ph); R$_{13}$=tBu: orange oil 8h R$_2$=CH$_2$(4-Ph-Ph); R$_3$=H; R$_4$=CH$_2$(4-Br-Ph); R$_{13}$=tBu: orange oil 8i R$_2$=CH$_3$; R$_3$=CH$_3$; R$_4$=CH$_2$(4-Br-Ph); R$_{13}$=Et: orange oil 8j R$_2$=C$_2$H$_5$; R$_3$=C$_2$H$_5$; R$_4$=CH$_2$(4-Br-Ph); R$_{13}$=Et: orange oil 8k C(R$_2$)(R$_3$)=Cyclopentyl; R$_4$=CH$_2$(4-Br-Ph); R$_{13}$=Et: orange oil 8l C(R$_2$)(R$_3$)=Cyclohexyl; R$_4$=CH$_2$(4-Br-Ph); R$_{13}$=Et: orange oil 8m C(R$_2$)(R$_3$)=Phenylcyclopentyl (Indanyl); R$_4$=CH$_2$(4-Br-Ph); R$_{13}$=Et: orange oil 1.1.4 Step 4

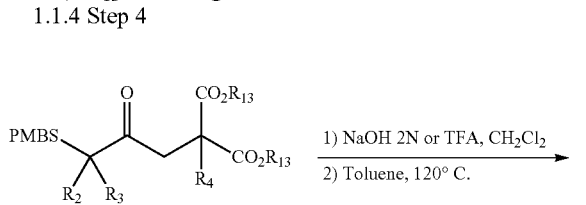

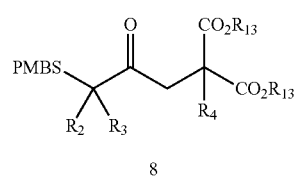

When R$_{13}$ is a methyl ethyl group, compound 8 (0.585 mmol) is dissolved in 10 ml of EtOH and 2 N NaOH (6 eq) is added. The mixture is stirred overnight at room temperature. The ethanol is evaporated under reduced pressure. The product is taken up in water and extracted with Et$_2$O. The aqueous phase is acidified with 3 N HCl and extracted with Et$_2$O. The organic phase is dried on Na$_2$SO$_4$ and then evaporated under reduced pressure to yield a yellow oil.

When R$_{13}$ is a tert-butyl group, product 8 is dissolved in 10 ml of CH$_2$Cl$_2$ and 10 ml of TFA is added. The mixture is stirred for 2 hours at room temperature. The solvents are evaporated under reduced pressure. The product is taken up in water and extracted with Et$_2$O. The organic phase is dried on Na$_2$SO$_4$ and then evaporated under reduced pressure to yield a yellow oil.

The product formed is then solubilized in 6 ml of toluene and heated to 150° C. for 12 hours. The solvent is evaporated under reduced pressure to yield compound 9.

9a R$_2$=CH$_2$Ph; R$_3$=H; R$_4$=CH$_2$(4-Br-Ph); orange oil
9b R$_2$=CH$_2$Ph; R$_3$=H; R$_4$=CH$_2$Ph; orange oil
9c R$_2$=CH$_2$CH(CH$_3$)$_2$; R$_3$=H; R$_4$=CH$_2$(4-Ph-Ph); orange oil
9d R$_2$=CH$_2$CH(CH$_3$)$_2$; R$_3$=H; R$_4$=CH$_2$Ph; orange oil
9e R$_2$=CH$_2$CH(CH$_3$)$_2$; R$_3$=H; R$_4$=CH$_2$(4-Br-Ph); orange oil
9f R$_2$=CH$_2$(4-Br-Ph); R$_3$=H; R$_4$=CH$_2$Ph; orange oil
9g R$_2$=CH$_2$(4-Br-Ph); R$_3$=H; R$_4$=CH$_2$(4-Br-Ph); orange oil
9h R$_2$=CH$_2$(4-Ph-Ph); R$_3$=H; R$_4$=CH$_2$(4-Br-Ph); orange oil
9i R$_2$=CH$_3$; R$_3$=CH$_3$; R$_4$=CH$_2$(4-Br-Ph); orange oil
9j R$_2$=C$_2$H$_5$; R$_3$=C$_2$H$_5$; R$_4$=CH$_2$(4-Br-Ph); orange oil
9k C(R$_2$)(R$_3$)=Cyclopentyl; R$_4$=CH$_2$(4-Br-Ph); orange oil
9l C(R$_2$)(R$_3$)=Cyclohexyl; R$_4$=CH$_2$(4-Br-Ph); orange oil
9m C(R$_2$)(R$_3$)=Phenylcyclopentyl (Indanyl); R$_4$=CH$_2$(4-Br-Ph); orange oil Suzuki Reaction

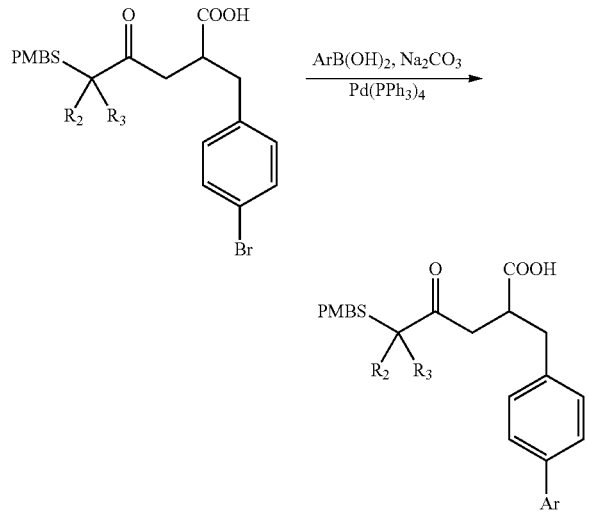

Compound 9l (180 mg; 0.356 mmol) is dissolved in 2 ml of toluene, under inert atmosphere. Pd(PPh$_3$)$_4$ (11 mg; 3% mol) is added and the mixture is stirred for 5 minutes at room temperature. Phenylboronic acid (46 mg; 0.374 mmol; 1.05 eq) is added to 1 ml of MeOH followed by 500 μl of 2 M Na$_2$CO$_3$. The mixture is refluxed for 1.5 hours and then the mixture is concentrated under reduced pressure. The reaction mixture is taken up in 30 ml of Et$_2$O and 30 ml of 1 N HCl. The organic phase is washed with 20 ml of 1 N HCl, 10 ml of saturated NaCl, dried on Na$_2$SO$_4$ and concentrated under reduced pressure. The product is purified by chromatography on silica with Hept/AcOEt 65/35 as elution system to yield the desired product 9n.

9n C(R$_2$)(R$_3$)=Cyclohexyl; R$_4$=CH$_2$(4-Ph-Ph); 75 mg orange oil (Yield: 47%)
ESI(+): [M+Na]$^+$=525.2
HPLC: Atlantis T3 CH$_3$CN(0.1% TFA)/H$_2$O (0.1% TFA) Gradient 70-90% 10 min,
Rt=8.60 min The following compounds are obtained according to an identical protocol.

9o C(R$_2$)(R$_3$)=Cyclopentyl; R$_4$=CH$_2$(4-Ph-Ph); orange oil (Yield: 25%)
ESI(−): [M−H]$^-$=487.2
HPLC: Atlantis T3 CH$_3$CN(0.1% TFA)/H$_2$O (0.1% TFA) Gradient 70-90% 10 min,
Rt=6.60 min 9p C(R$_2$)(R$_3$)=PhenylCyclopentyl (Indanyl); R$_4$=CH$_2$(4-Ph-Ph); orange oil
(Yield: 55%)
ESI(−): [M−H]$^-$=535.2
HPLC: Atlantis T3 CH$_3$CN(0.1% TFA)/H$_2$O (0.1% TFA) Gradient 70-90% 10 min,
Rt=7.45 min 1.1.5 Step 5:

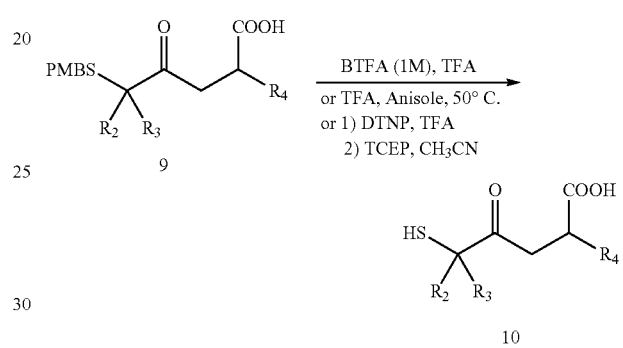

Method 1: Compound 9 (0.53 mmol) of step 7 is solubilized in 2.1 ml of BTFA (boron tristrifluoroacetate) (1 M) (prepared beforehand from BBr$_3$ and TFA) and stirred for 1 hour at room temperature. The solvents are evaporated under reduced pressure and the mixture is purified by semi-preparative HPLC.

10a R$_2$=CH$_2$Ph; R$_3$=H; R$_4$=CH$_2$Ph
ESI(+): [M+H]$^+$=329
HPLC: ACE C18 CH$_3$CN/H$_2$O (0.1% TFA) Gradient 60/90 in 30 min; Rt: 7.50 min 10b R$_2$=iBu; R$_3$=H; R$_4$=CH$_2$(4-Br-Ph)
ESI(+): [M+H]$^+$=372 and 374
HPLC: ACE C18 CH$_3$CN/H$_2$O (0.1% TFA) Gradient 60/90 in 30 min; Rt: 8.60 min 10c R$_2$=CH$_2$(4-Br-Ph); R$_3$=H; R$_4$=CH$_2$(4-Br-Ph)
ESI(+): [M+H]$^+$=384
HPLC: ACE C18 CH$_3$CN/H$_2$O (0.1% TFA) Gradient 60/90 in 30 min; Rt: 10.52 min 10d R$_2$=CH$_2$(4-Br-Ph); R$_3$=H; R$_4$=CH$_2$Ph
ESI(+): [M+H]$^+$=406 and 408
HPLC: ACE C18 CH$_3$CN/H$_2$O (0.1% TFA) Gradient 60/90 in 30 min; Rt: 9.01 min 10e R$_2$=CH$_2$Ph; R$_3$=H; R$_4$=CH$_2$(4-Br-Ph)
ESI(+): [M+H]$^+$=406 and 408
HPLC: Kromasil C18 CH$_3$CN/H$_2$O (0.1% TFA) 80/20; Rt: 6.23 min 10f R$_2$=CH$_2$(4-Ph-Ph); R$_3$=H; R$_4$=CH$_2$(4-Br-Ph)
ESI(+): [M+H]$^+$=482 and 484
HPLC: ACE C18 CH$_3$CN/H$_2$O (0.1% TFA) Gradient 60/90 in 30 min; Rt: 11.4 min Method 2: Product 9c (2.03 mmol) is solubilized in 10 ml of TFA in the presence of 5 eq of anisole (1.1 ml). The mixture is heated for 2.5 hours at 50° C. The solvents are evaporated under reduced pressure and the mixture is purified by semi-preparative HPLC to yield compound 10b.

10b $R_2$=iBu; $R_3$=H; $R_4$=$CH_2$(4-Br-Ph)
ESI(+): [M+H]$^+$=372 and 374
HPLC: ACE C18 $CH_3CN/H_2O$ (0.1% TFA) Gradient 60/90 in 30 min; Rt: 8.60 min Method 3: To a solution, under inert atmosphere, of compound 9c (0.447 mmol; 120 mg) in 4.5 ml of TFA is added thioanisole (2.8 eq; 0.936 mmol; 110 µl) followed by the addition of 2,2'-dithiobis(5-nitropyridine) (3 eq; 1.0 mmol; 417 mg): the solution becomes orange. The mixture is stirred at room temperature for 1 hour. The mixture is concentrated under reduced pressure at 30° C. The disulfide formed is purified by semi-preparative HPLC to yield 146 mg of product (Yield: 62%).

The preceding disulfide is solubilized in $CH_3CN$ (720 µl)/$H_2O$ (180 µl). Tris(2-carboxyethyl)phosphine hydrochloride (1.2 eq; 96 mg) is then added and the mixture is stirred for 10 minutes at room temperature. The solvents are evaporated under reduced pressure and the compound is purified by semi-preparative HPLC to yield 10b. This synthesis scheme preserves the chirality of the molecule, if it exists.

10b $R_2$=iBu; $R_3$=H; $R_4$=$CH_2$(4-Br-Ph)
ESI(+): [M+H]$^+$=372 and 374
HPLC: ACE C18 $CH_3CN/H_2O$ (0.1% TFA) 60/90 in 30 min; Rt: 8.60 min
NMR ($CDCl_3$, 200 MHz): 0.87 (3H, d); 0.89 (3H, d); 1.50-1.80 (3H, m); 2.7-3.5 (6H, m); 7.08 (2H, d); 7.43 (2H, d)

The following compounds are obtained according to an identical protocol.

10g $R_2$=$CH_3$; $R_3$=$CH_3$; $R_4$=$CH_2$(4-Br-Ph)
ESI(+): [M+Na]$^+$=366 and 368
HPLC: Atlantis T3 $CH_3CN/H_2O$ (0.1% TFA) 50/90 in 10 min; Rt: 6.51 min
NMR (DMSO d6, 200 MHz): 1.45 (3H, s); 1.47 (3H, s); 2.7-3.2 (5H, m); 7.18 (2H, d); 7.50 (2H, d)

10h $R_2$=$C_2H_5$; $R_3$=$C_2H_5$; $R_4$=$CH_2$(4-Br-Ph)
ESI(+): [M+Na]$^+$=394 and 396
HPLC: Atlantis T3 $CH_3CN/H_2O$ (0.1% TFA) 70/90 in 10 min; Rt: 3.9 min
NMR ($CDCl_3$, 200 MHz): 1.30 (6H, t); 1.75 (4H, q); 2.6-3.1 (5H, m); 7.0 (2H, d); 7.40 (2H, d)

10i $C(R_2)(R_3)$=$C_5H_8$; $R_4$=$CH_2$(4-Br-Ph)
ESI(+): [M+H]$^+$=370 and 372
HPLC: Atlantis T3 $CH_3CN/H_2O$ (0.1% TFA) 60/90 in 10 min; Rt: 5.0 min
NMR ($CDCl_3$, 200 MHz): 1.60-2.25 (8H, m); 2.75-3.20 (5H, m); 7.10 (2H, d); 7.44 (2H, d)

10j $C(R_2)(R_3)$=$C_6H_{10}$; $R_4$=$CH_2$(4-Br-Ph)
ESI(+): [M+Na]$^+$=382 and 384
HPLC: Atlantis T3 $CH_3CN/H_2O$ (0.1% TFA) 70/90 in 10 min; Rt: 8.97 min
NMR ($CDCl_3$, 200 MHz): 1.60-2.40 (10H, m); 2.75-3.20 (5H, m); 7.10 (2H, d); 7.44 (2H, d)

10k $C(R_2)(R_3)$=$C_9H_8$; $R_4$=$CH_2$(4-Br-Ph)
ESI(+): [M+Na]$^+$=442 and 444
HPLC: Atlantis T3 $CH_3CN/H_2O$ (0.1% TFA) 70/90 in 10 min; Rt: 3.84 min
NMR ($CDCl_3$, 200 MHz): 2.70-3.50 (5H, m); 3.60 (2H, d); 3.70 (2H, d); 7.10-7.6 (8H, m)

10l $C(R_2R_3)$=$C_6H_{10}$; $R_4$=$CH_2$(4-Ph-Ph)
ESI(+): [M+H]$^+$=383
HPLC: Atlantis T3 $CH_3CN/H_2O$ (0.1% TFA) 70/90 in 10 min; Rt: 5.35 min
NMR ($CDCl_3$, 200 MHz): 1.60-2.40 (10H, m); 2.75-3.20 (5H, m); 7.20-7.60 (9H, m)

10m $C(R_2R_3)$=$C_5H_8$; $R_4$=$CH_2$(4-Br-Ph)
ESI(+): [M+H]$^+$=368 and 370
HPLC: Atlantis T3 $CH_3CN/H_2O$ (0.1% TFA) 60/40; Rt: 9.79 min
NMR ($CDCl_3$, 200 MHz): 1.60-2.25 (8H, m); 2.75-3.20 (5H, m); 7.05-7.55 (9H, m)

10n $C(R_2)(R_3)$=$C_9H_8$; $R_4$=$CH_2$(4-Ph-Ph)
ESI(+): [M+H]$^+$=415
HPLC: Atlantis T3 $CH_3CN/H_2O$ (0.1% TFA) 70/90 in 10 min; Rt: 4.73 min
NMR ($CDCl_3$, 200 MHz): 2.70-3.50 (5H, m); 3.60 (2H, d); 3.70 (2H, d); 7.10-7.8 (13H, m)

1.2 Synthesis of Mixt NEP-APN Inhibitors 1.2.1 Synthesis of Boc-Beta-Aminothiol 11

The compounds are prepared by following the protocol described in *J. Med. Chem.*, 35, 1992, 2473.

11a $R_1$: $CH_2CH_2SCH_3$; White solid
HPLC: Atlantis T3, $CH_3CN$(0.1% TFA)/$H_2O$ (0.1% TFA) Gradient 50-90% 10 min, Rt=6.45 min
NMR ($CDCl_3$, 200 MHz): 1.45 (9H, s); 1.85 (2H, m); 2.12 (3H, s); 2.52 (2H, t); 2.75 (2H, dd); 3.90 (1H, t); 4.80 (1H, NH)

11b $R_1$: $CH_2CH_2CH_2CH_3$; White solid
HPLC: ACE C18, $CH_3CN$(0.1% TFA)/$H_2O$ (0.1% TFA) 30%-70%, Rt=13.53 min
NMR (DMSO d6, 200 MHz): 0.95 (3H, t); 1.20-1.60 (6H, m); 1.40 (9H, s); 2.30 (2H, m); 3.40 (1H, t); 6.80 (1H, NH)

11c $R_1$: $CH_2CH_2O\,CH_3$; White solid
HPLC: ACE C18, $CH_3CN$(0.1% TFA)/$H_2O$ (0.1% TFA) 50%-50%, Rt=5.58 min
NMR (DMSO d6, 200 MHz): 1.40 (9H, s); 1.60 (2H, m); 2.75-3.10 (2H, m); 3.20 (3H, s); 3.30 (2H, t); 3.60 (1H, m); 6.80 (1H, NH)

11d $R_1$: $CH_2CH_2O\,CH_2CH_3$; White solid
HPLC: ACE C18, $CH_3CN$(0.1% TFA)/$H_2O$ (0.1% TFA) 40%-60%, Rt=13.33 min
NMR (DMSO d6, 200 MHz): 1.10 (3H, t); 1.40 (9H, s); 1.60 (2H, m); 2.60 (2H, m); 3.10-3.30 (2H, m); 3.30 (2H, q); 3.60 (1H, m); 6.80 (1H, NH)

11e $R_1$: $CH_2O\,CH_2CH_3$; White solid
HPLC: ACE C18, $CH_3CN$(0.1% TFA)/$H_2O$ (0.1% TFA) 40%-60%, Rt=14.00 min
NMR (DMSO d6, 200 MHz): 1.10 (3H, t); 1.40 (9H, s); 3.20-3.40 (4H, m); 3.30 (2H, q); 3.60 (1H, m); 6.70 (1H, NH)

1.2.2 Synthesis of Dissymmetrical Disulfide 12

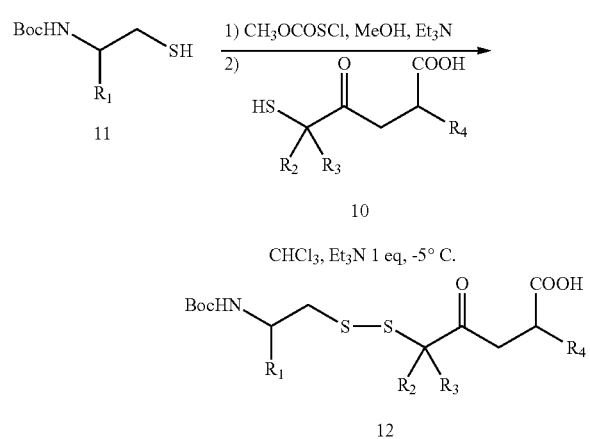

Boc-aminothiol thiol 11 (9.86 mmol, 2.5 g) is dissolved at 0° C., under inert atmosphere, in 20 ml of degassed MeOH. $Et_3N$ (2 eq; 2.79 ml) is added followed by methoxycarbonylsulfonic acid chloride (2 eq, 1.78 ml) in solution in 20 ml of degassed $CHCl_3$. The mixture is stirred for 15 minutes at 0° C. and then 100 ml of $CHCl_3$ is added. The organic phase is washed with 10% citric acid (2×100 ml), $H_2O$ (100 ml), saturated NaCl (100 ml), dried on $Na_2SO_4$ and concentrated under reduced pressure. The product is purified on silica gel.

$R_1$: $CH_2CH_2SCH_3$; White solid (Yield: 40%)
HPLC: Atlantis T3, $CH_3CN$(0.1% TFA)/$H_2O$ (0.1% TFA) Gradient 70-90% in 10 min, Rt=3.66 min
NMR ($CDCl_3$, 200 MHz): 1.45 (9H, s); 1.85 (2H, m); 2.12 (3H, s); 2.52 (2H, t); 2.75 (2H, dd); 3.90 (1H, t); 3.90 (3H, s); 5.0 (1H, NH)

$R_1$: $CH_2CH_2CH_2CH_3$; White solid (Yield: 41%)
HPLC: Atlantis T3, $CH_3CN$(0.1% TFA)/$H_2O$ (0.1% TFA) Gradient 70-90% in 10 min, Rt=5.57 min
NMR ($CDCl_3$, 200 MHz): 0.90 (3H, t); 1.34 (4H, m); 1.45 (9H, s); 1.62 (2H, m); 2.99 (2H, d); 3.78 (1H, m); 3.90 (3H, s); 4.77 (1H, NH)

Compound 10 is added to a solution of the preceding compound (0.754 mmol, 1 eq) in 8 ml of degassed $CHCl_3$, under inert atmosphere. The mixture is cooled to −10° C. and degassed $Et_3N$ (0.754 mmol, 105 µl, 1 eq) is added. The mixture is stirred for 30 minutes at −10° C. and then diluted with 10 ml of $CH_2Cl_2$. The organic phase is washed with 10% citric acid (5 ml), saturated NaCl (2×10 ml), dried on $Na_2SO_4$ to yield a crude product, which is purified by semi-preparative HPLC to yield compound 12.

12a-b $R_1$: $CH_2CH_2SCH_3$; $R_2$: iBu; $R_3$: H; $R_4$: $CH_2$(4-Br-Ph) (Yield: 64%)
ESI(+): [M+Na]$^+$=644 and 646

12b-b $R_1$: $CH_2CH_2CH_2CH_3$; $R_2$: iBu; $R_3$: H; $R_4$: $CH_2$(4-Br-Ph) (Yield: 87%)
ESI(+): [M+Na]$^+$=626 and 628

12b-l $R_1$: $CH_2CH_2CH_2CH_3$; $C(R_2R_3)$: $C_6H_{10}$; $R_4$: $CH_2$(4-Ph-Ph) (Yield: 85%)
ESI(+): [M+Na]$^+$=637

12b-j $R_1$: $CH_2CH_2CH_2CH_3$; $C(R_2R_3)$: $C_6H_{10}$; $R_4$: $CH_2$(4-Br-Ph) (Yield: 90%)
ESI(+): [M+Na]$^+$=638 and 640

12a-l $R_1$: $CH_2CH_2SCH_3$; $C(R_2R_3)$: $C_6H_{10}$; $R_4$: $CH_2$(Ph-Ph) (Yield: 90%)
ESI(+): [M+H]$^+$=632

1.2.3 Preparation of Compounds 1
Method 1:
Part 1: Synthesis of Esters

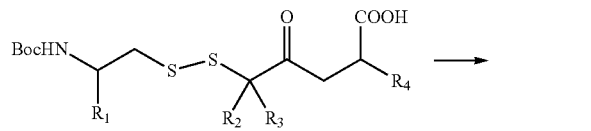

12

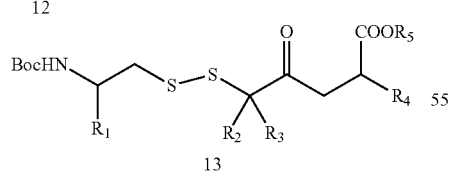

13

Compound 13a-b-1: 1-(ethoxycarbonyloxy)ethyl 2-(4-bromobenzyl)-5-(((S)-2-(tert-butoxycarbonylamino)-4-(methylthio)butyl)disulfanyl)-7-methyl-4-oxooctanoate Compound 12a-b (640 mg; 1.03 mmol) and $Et_3N$ (730 µl, 5 eq) are dissolved in 10 ml of AcOEt. The mixture is stirred for 15 minutes at room temperature. Ethyl-1-chloroethylcarbonate (prepared according to Barcelo et al. *Synthesis,* 1986, 627) (800 µl; 5 eq) and NaI (800 mg, 5 eq) are added. The mixture is refluxed for 3 hours. The mixture is diluted with 10 ml of $H_2O$ and 20 ml of AcOEt. The aqueous phase is extracted with 3×30 ml of AcOEt. The organic phase is washed with 10% citric acid (2×15 ml), 10% $NaHCO_3$ (2×15 ml), saturated NaCl, dried on $Na_2SO_4$ and is evaporated under reduced pressure to yield a crude product. The mixture is purified by semi-preparative HPLC to yield 80 mg of a yellow oil.

13a-b-1 $R_1$: $CH_2CH_2SCH_3$; $R_2$: iBu; $R_3$: H; $R_4$: $CH_2$(4-Br-Ph); $R_5$:
$CH(CH_3)OCOOC_2H_5$ (Yield 10.5%)
HPLC: Atlantis T3, $CH_3CN$(0.1% TFA)/$H_2O$ (0.1% TFA) Gradient 70-90% in 10 min, Rt=12.85 min
ESI(+): [M+Na]$^+$=760 and 762

Compound 13b-b-1: ethyl 2-(4-bromobenzyl)-5-(((S)-2-(tert-butoxycarbonylamino) hexyl)disulfanyl)-7-methyl-4-oxooctanoate Compound 12b-b (395 mg; 0.653 mmol) is dissolved at 4° C., under inert atmosphere, in 4.3 ml of $CH_2Cl_2$. EDCl-HCl (138 mg; 0.718 mmol; 1.1 eq) is added, followed by DMAP (88 mg; 0.718 mmol; 1.1 eq) and EtOH (0.784 mmol; 1.2 eq). The mixture is stirred for 4 hours at room temperature. The mixture is diluted with 10 ml of 10% citric acid and 20 ml of $CH_2Cl_2$. The organic phase is washed with 10% citric acid (2×10 ml), 10% $NaHCO_3$ (2×10 ml), saturated NaCl, dried on $Na_2SO_4$ and evaporated under reduced pressure to yield a crude product. The mixture is purified by semi-preparative HPLC to yield a yellow oil.

13b-b-1 $R_1$: $CH_2CH_2CH_2CH_3$; $R_2$: iBu; $R_3$: H; $R_4$: $CH_2$(4-Br-Ph); $R_5$: $C_2H_5$ (Yield 60%)
HPLC: Atlantis T3, $CH_3CN$(0.1% TFA)/$H_2O$ (0.1% TFA) Gradient 80-90% in 10 min, Rt=12.20-12.65 min Part 2: Deprotection of the Amine

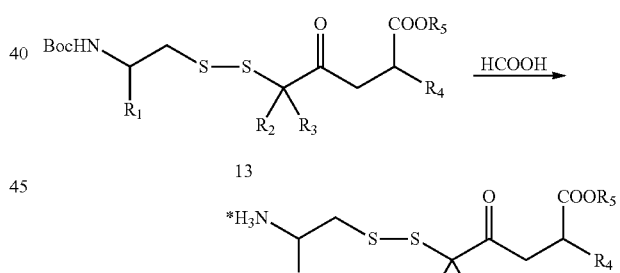

Compound 1a-b-1: 1-(ethoxycarbonyloxy)ethyl 5-(((S)-2-amino-4-(methylthio)butyl)disulfanyl)-2-(4-bromobenzyl)-7-methyl-4-oxooctanoate Compound 13a-b-1 (130 mg; 0.176 mmol) is stirred in 2 ml of HCOOH for 1 hour. The mixture is evaporated under reduced pressure to yield a crude product which is purified by semi-preparative HPLC to yield 13 mg of compound 1a-b-1.

1a-b-1 $R_1$: $CH_2CH_2SCH_3$; $R_2$: iBu; $R_3$: H; $R_4$: $CH_2$(4-Br-Ph); $R_5$:
$CH(CH_3)OCOOC_2H_5$ (Yield 11%)
HPLC: Atlantis T3, $CH_3CN$(0.1% TFA)/$H_2O$ (0.1% TFA) Gradient 10-90% in 15 min, Rt=14.50 min
ESI(+): [M+H]$^+$=638 and 640

Compound 1b-b-1: ethyl 5-(((S)-2-aminohexyl)disulfanyl)-2-(4-bromobenzyl)-7-methyl-4-oxooctanoate Compound 13b-b-1 (141 mg; 0.223 mmol) is stirred in 2 ml of HCOOH for 1 hour. The mixture is evaporated under reduced pressure to yield a crude product which is purified by semi-preparative HPLC to yield 92 mg of compound 1 b-b-1.

1b-b-1 $R_1$: $CH_2CH_2CH_2CH_3$; $R_2$: iBu; $R_3$: H; $R_4$: $CH_2$(4-Br-Ph); $R_5$: $C_2H_5$ (Yield 64%)
HPLC: Atlantis T3, $CH_3CN$(0.1% TFA)/$H_2O$ (0.1% TFA) Gradient 50-90% in 10 min, Rt=7.79 min
ESI(+): $[M+H]^+$=532 and 534

Compound 1f-b-1: ethyl 5-((2-amino-4-(methylsulfinyl)butyl)disulfanyl)-2-(4-bromobenzyl)-7-methyl-4-oxooctanoate 1f-b-1 $R_1$: $CH_2CH_2SOCH_3$; $R_2$: iBu; $R_3$: H; $R_4$: $CH_2$(4-Br-Ph); $R_5$: $C_2H_5$ (Yield 47.9%)
HPLC: Atlantis T3, $CH_3CN$(0.1% TFA)/$H_2O$ (0.1% TFA) Gradient 10-90% in 15 min, Rt=12.45 min
ESI(+): $[M+H]^+$=566 and 568
Method 2:

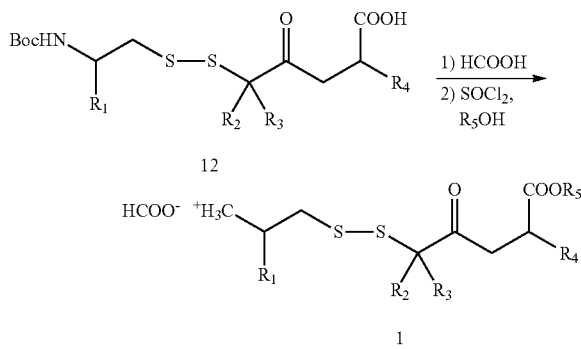

Compound 12 (0.323 mmol) is stirred in 4 ml of HCOOH for 1 hour. The mixture is evaporated under reduced pressure to yield a crude product which is purified by semi-preparative HPLC to yield the acid.

$R_1$: $CH_2CH_2SCH_3$; $R_2$: iBu; $R_3$: H; $R_4$: $CH_2$(4-Br-Ph) (Yield 69%)
HPLC: ACE C18, $CH_3CN$(0.1% TFA)/$H_2O$ (0.1% TFA) 60/40%, Rt=8.0 min
ESI(+): $[M+H]^+$=522 and 524

$R_1$: $CH_2CH_2CH_2CH_3$; $C(R_2)(R_3)$: $C_6H_{10}$; $R_4$: $CH_2$(4-Ph-Ph) (Yield 60%)
HPLC: Luna T3, $CH_3CN$(0.1% TFA)/$H_2O$ (0.1% TFA) 60/40%, Rt=2.83 min
ESI(+): $[M+H]^+$=514
$R_1$: $CH_2CH_2CH_2CH_3$; $C(R_2)(R_3)$: $C_6H_{10}$; $R_4$: $CH_2$(4-Br-Ph) (Yield 69%)
HPLC: ACE C18, $CH_3CN$(0.1% TFA)/$H_2O$ (0.1% TFA) 60/40%, Rt=8.0 min
ESI(+): $[M+H]^+$=516 and 518
$R_1$: $CH_2CH_2SCH_3$; $C(R_2)(R_3)$: $C_6H_{10}$; $R_4$: $CH_2$(4-Ph-Ph) (Yield 70%)
HPLC: Luna C18, $CH_3CN$(0.1% TFA)/$H_2O$ (0.1% TFA) 50/50%, Rt=5.43 min
ESI(+): $[M+H]^+$=532

$SOCl_2$ (30 μl, 6 eq) is added to a suspension of the preceding acid (0.068 mmol) at 0° C., under inert atmosphere, in 400 μl of anhydrous EtOH ($R_5$=Et). The solution becomes clear. The mixture is stirred overnight at room temperature. The mixture is evaporated under reduced pressure to yield a crude product which is purified by semi-preparative HPLC to yield 35 mg of the expected product.

1a-b-2 $R_1$: $CH_2CH_2SCH_3$; $R_2$: iBu; $R_3$: H; $R_4$: $CH_2$(4-Br-Ph); $R_5$: $C_2H_5$ (Yield 82%)
HPLC: ACE C18, $CH_3CN$(0.1% TFA)/$H_2O$ (0.1% TFA) Gradient 50/90% in 30 min, Rt=11.98 min
ESI(+): $[M+H]^+$=550 and 552
1b-l-1 $R_1$: $CH_2CH_2CH_2CH_3$; $C(R_2)(R_3)$: $C_6H_{10}$; $R_4$: $CH_2$(4-Ph-Ph); $R_5$: $C_2H_5$ (Yield 80%)
HPLC: Atlantis T3, $CH_3CN$(0.1% TFA)/$H_2O$ (0.1% TFA) Gradient 70/90% in 10 min, Rt=4.0 min
ESI(+): $[M+H]^+$=542
1b-j-1 $R_1$: $CH_2CH_2CH_2CH_3$; $C(R_2)(R_3)$: $C_6H_{10}$; $R_4$: $CH_2$(4-Br-Ph); $R_5$: $C_2H_5$ (Yield 85%)
HPLC: Atlantis T3, $CH_3CN$(0.1% TFA)/$H_2O$ (0.1% TFA) Gradient 70/90% in 10 min, Rt=3.28 min
ESI(+): $[M+H]^+$=546 and 548
1a-l-1 $R_1$: $CH_2CH_2SCH_3$; $C(R_2)(R_3)$: $C_6H_{10}$; $R_4$: $CH_2$(4-Ph-Ph); $R_5$: $C_2H_5$ (Yield 86%)
HPLC: Atlantis T3, $CH_3CN$(0.1% TFA)/$H_2O$ (0.1% TFA) Gradient 50/90% in 10 min, Rt=8.42 min
ESI(+): $[M+H]^+$=560
1b-l-2 $R_1$: $CH_2CH_2CH_2CH_3$; $C(R_2)(R_3)$: $C_6H_{10}$; $R_4$: $CH_2$(4-Ph-Ph); $R_5$: $CH_2$Ph (Yield 71%)
HPLC: Atlantis T3, $CH_3CN$(0.1% TFA)/$H_2O$ (0.1% TFA) Gradient 70/90% in 10 min, Rt=5.71 min
ESI(+): $[M+H]^+$=604
Method 3:

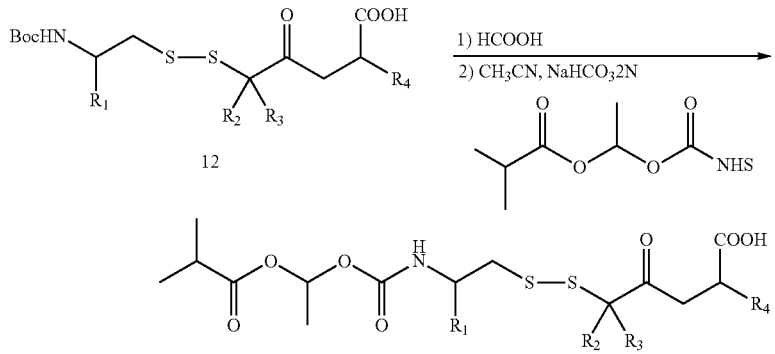

Compound 1b-1-3: 2-(biphenyl-4-ylmethyl)-4-(1-((2-((1-(isobutyryloxy)ethoxy)carbonylamino)(S)-hexyl)disulfanyl)cyclohexyl)-4-oxobutanoic acid Compound 12b-1 (590 mg; 0.961 mmol) is stirred in 10 ml of HCOOH for 1 hour. The mixture is evaporated under reduced pressure to yield a crude product which is purified by semi-preparative HPLC to yield the 2 diastereoisomers.

$R_1$: $CH_2CH_2CH_2CH_3$; $C(R_2R_3)$: $C_6H_{10}$; $R_4$: $CH_2$(4-Ph-Ph) (Yield 89%)

HPLC Dia 1: Luna C18, $CH_3CN$ (0.1% TFA)/$H_2O$ (0.1% TFA) 55/35%, Rt=3.90 min

HPLC Dia 2: Luna C18, $CH_3CN$ (0.1% TFA)/$H_2O$ (0.1% TFA) 55/35%, Rt=4.10 min

ESI(+): $[M+H]^+$=522.2

The preceding compound (155 mg, 0.246 mmol) is solubilized in 2 ml of anhydrous $CH_3CN$. 370 µl of 2 N $NaHCO_3$ is added, followed by 1 ml of $H_2O$. The mixture is stirred for 10 minutes at RT and 1-((2,5-dioxopyrrolidin-1-yloxy)carbonyloxy)ethyl isobutyrate (90 mg; 0.329 mmol; 1 eq) (Cundy et al. (2004) *J. Pharm. Exp. Therap.*, 311, 315-323) in $CH_3CN$ (1 ml) is added. The mixture is stirred for 30 minutes at 60° C. The solvent is evaporated under reduced pressure. The product is taken up in AcOEt, 1 N HCl. The organic phase is washed, dried on $Na_2SO_4$, and concentrated under reduced pressure to yield a crude product which is purified by semi-preparative HPLC to yield the expected product.

1b-1-3 dia 1 $R_1$: $CH_2CH_2CH_2CH_3$; $C(R_2)(R_3)$: $C_6H_{10}$; $R_4$: $CH_2$(4-Ph-Ph) (Yield 85%)

HPLC: Atlantis T3, $CH_3CN$(0.1% TFA)/$H_2O$ (0.1% TFA) Gradient 70/90% in 15 min, Rt=10.50 min and 10.80 min

ESI(+): $[M+H]^+$=672.1

1b-1-3 dia 2 $R_1$: $CH_2CH_2CH_2CH_3$; $C(R_2)(R_3)$: $C_6H_{10}$; $R_4$: $CH_2$(4-Ph-Ph) (Yield 85%)

HPLC: Atlantis T3, $CH_3CN$(0.1% TFA)/$H_2O$ (0.1% TFA) Gradient 70/90% in 15 min, Rt=10.80 min and 11.10 min

ESI(+): $[M+H]^+$=672.1

2. Measurement of Inhibitory Strengths

Assays are carried out in 96-well plates in the presence of a specific fluorogenic substrate.

The emitted fluorescence is read in a Berthold Twinkle LS970B plate reader. A plot of inhibition as a function of inhibitor concentration is then created using the GraphPad software, then Ki is determined from the Cheng Prusoff formula:

$$Ki = IC_{50}/(1+(S/Km)).$$

Inhibitory strengths on the 2 target enzymes are determined:

From pro-drugs 1 after in situ cleavage of the N- and/or C-terminal protections and the disulfide bridge The preceding values are verified from intermediate selective inhibitors in the synthesis of pro-drugs, i.e., compounds 10 for neprilysin and 11, after deprotection of the amine functional group, for APN.

Inhibition of Neprilysin (NEP) Activity

Neprilysin purified from rabbit kidney (Aubry M. et al. 1987, *Biochem. Cell. Biol.* 65, 398-404) is used at a final concentration of 200 ng/ml in 50 mM Tris buffer, pH 7.4. The substrate, Dansyl-Gly-($NO_2$)Phe-β-Ala (Goudreau N. et al. (1994) *Anal. Biochem.*, 219, 87-95) (Km=37 µM), is dissolved in ethanol and used at a final concentration of 20 µM. Increasing concentrations (from $10^{-10}$ to $10^{-3}$ M) of inhibitors are preincubated with NEP-1 for 15 minutes at 37° C. in 50 mM Tris buffer, pH 7.4. The substrate is then added and incubation is continued for 60 minutes. The reaction is quenched by placing the plate in ice for 10 minutes. The emitted fluorescence is read in a fluorometer with λex=355 nm, λem=535 nm. The results are presented in the following tables.

| Compound | | $R_2$ | $R_3$ | $R_4$ | $R_5$ | NEP-1 Ki (nM) |
|---|---|---|---|---|---|---|
| 10 a | Dia 1 + Dia 2 | $CH_2Ph$ | H | $CH_2Ph$ | OH | 73 ± 8 |
| 10 a | Dia 3 + Dia 4 | $CH_2Ph$ | H | $CH_2Ph$ | OH | 1500 ± 200 |
| 10 b | 4 Dia | iBu | H | $CH_2$(4-Br—Ph) | OH | 20 ± 5 |
| 10 c | Dia 1 + Dia 2 | $CH_2$(4-Br—Ph) | H | $CH_2$(4-Br—Ph) | OH | 310 ± 25 |
| 10 c | Dia 3 + Dia 4 | $CH_2$(4-Br—Ph) | H | $CH_2$(4-Br—Ph) | OH | 130 ± 40 |
| 10 d | Dia 1 + Dia 2 | $CH_2$(4-Br—Ph) | H | $CH_2Ph$ | OH | 2300 ± 300 |
| 10 d | Dia 3 + Dia 4 | $CH_2$(4-Br—Ph) | H | $CH_2Ph$ | OH | 1230 ± 300 |
| 10 e | 4 Dia | $CH_2Ph$ | H | $CH_2$(4-Br—Ph) | OH | 50 ± 8 |
| 10 f | 4 Dia | $CH_2$(4-Ph—Ph) | H | $CH_2$(4-Br—Ph) | OH | 250 ± 50 |
| 10 g | 2 stereo | $CH_3$ | $CH_3$ | $CH_2$(4-Br—Ph) | OH | 470 ± 40 |
| 10 h | 2 stereo | $C_2H_5$ | $C_2H_5$ | $CH_2$(4-Br—Ph) | OH | 86 ± 9 |
| 10 i | 2 stereo | 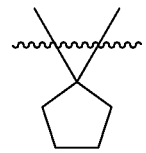 | | $CH_2$(4-Br—Ph) | OH | 52 ± 4 |
| 10 j | 2 stereo | 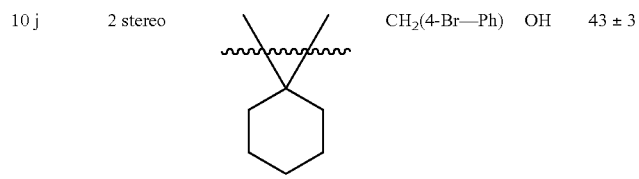 | | $CH_2$(4-Br—Ph) | OH | 43 ± 3 |

| Compound | R₂ | R₃ | R₄ | R₅ | NEP-1 Ki (nM) |
|---|---|---|---|---|---|
| 10 k | 2 stereo | 2,2-indanyl | | $CH_2$(4-Br—Ph) | OH | 36 ± 3 |
| 10 l | 2 stereo | 1,1-cyclohexyl | | $CH_2$(4-Ph—Ph) | OH | 9 ± 1 |
| 10 m | 2 stereo | 1,1-cyclopentyl | | $CH_2$(4-Ph—Ph) | OH | 29 ± 5 |
| 10 n | 2 stereo | 2,2-indanyl | | $CH_2$(4-Ph—Ph) | OH | 26 ± 1 |

| Compound | R₂ | R₃ | R₄ | R₅ | NEP-1 Ki (nM) |
|---|---|---|---|---|---|
| 10 b | Dia 1 | (R or S)—iBu | H | (R)—$CH_2$(4-Br—Ph) | OH | 15 ± 1 |
| 10 b | Dia 2 | (R or S)—iBu | H | (R)—$CH_2$(4-Br—Ph) | OH | 12 ± 0.5 |
| 10 b | Dia 3 | (R or S)—iBu | H | (S)—$CH_2$(4-Br—Ph) | OH | 6 ± 0.5 |
| 10 b | Dia 4 | (R or S)—iBu | H | (S)—$CH_2$(4-Br—Ph) | OH | 5 ± 0.4 |
| 10 l | Stereo 1 | 1,1-cyclohexyl | | (R)—$CH_2$(4-Ph—Ph) | OH | 4.2 ± 0.1 |
| 10 l | Stereo 2 | 1,1-cyclohexyl | | (S)—$CH_2$(4-Ph—Ph) | OH | 36 ± 0.7 |

Inhibition of APN Activity

Inhibition of aminopeptidase N (APN) is measured by the use of the L-Ala↓β-NA substrate (50 μM, Sigma Aldrich). Inhibitory strengths are determined using recombinant human enzyme (Rh) (50 ng/ml; R&D System). Increasing concentrations (from $10^{-10}$ to $10^{-3}$ M) of inhibitors are pre-incubated for 30 minutes at 37° C. with APN-Rh in 50 mM Tris buffer, pH 7.4. The substrate is then added and incubation is continued for 30 minutes at 37° C. The reaction is quenched by placing the plate in ice for 10 minutes. The emitted fluorescence is read in a fluorometer with λex=340 nm, λem=405 nm. The results are presented in the following table.

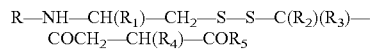

| Compound | $R_1$ | Ki APN (nM) |
|---|---|---|
| a | $CH_2CH_2SCH_3$ | 11 ± 2 |
| b | $CH_2CH_2CH_2CH_3$ | 13 ± 2 |
| c | $CH_2CH_2OCH_3$ | 35 ± 2 |
| d | $CH_2CH_2OCH_2CH_3$ | 47 ± 8 |
| e | $CH_2OCH_2CH_3$ | 55 ± 10 |

3. Pharmacology: Hot Plate Test

The jumping reflex in a mouse placed on a plate heated at 52° C. is measured by the time taken by the animal to jump in order to escape pain (jump latency) (Eddy, N. B et al. *J. Pharm. Exp. Therap.*, 1953, 107, 385-389). The compound of formula (1a-b-1 Dia 3) or (1 b-l-1 Dia 1) is injected intravenously in male OF1 mice (23-26 g) (10 mg/kg) after dissolution in a mixture of ethanol/tween 80/water (1/1/8).

Injection volume: 10 ml/kg

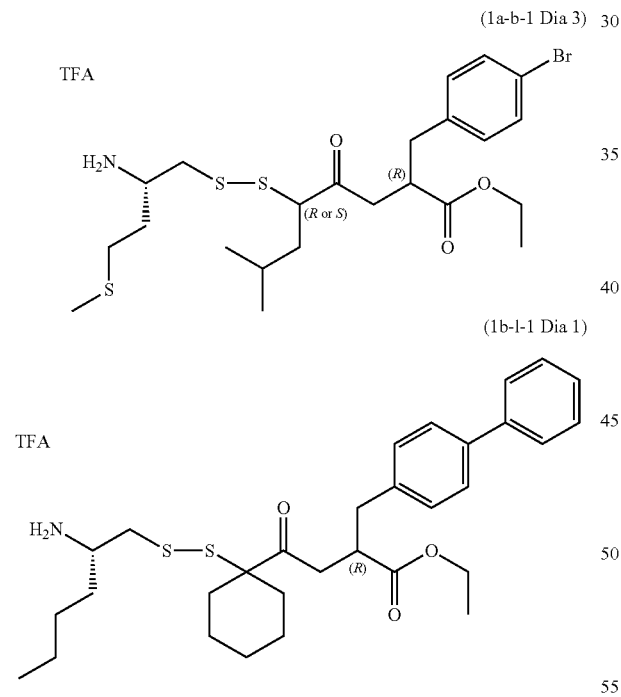

Jump latency times are measured 10 minutes after the intravenous injections. The results are expressed as percentage of analgesia using the following equation:

% analgesia=(measured latency time−control latency time)

(maximum latency time−control latency time)

Maximum latency time=240 seconds.

The results are expressed in terms of mean±SEM. The results are presented in FIG. 1.

The invention claimed is:

1. A compound of formula (1)

$$R-NH-CH(R_1)-CH_2-S-S-C(R_2)(R_3)-COCH_2-CH(R_4)-COR_5 \quad (1)$$

wherein a) R is:
   hydrogen; or
   an alkoxyalkylcarbonyl group R'C(O)OCH(R")OC(O)— where R' and R" are, independently, an alkyl group containing 1 to 6 carbon atoms;

b) $R_1$ is a linear or branched alkyl group of 1 to 6 carbon atoms, substituted, or not, by an —OR'", —SOR'" or —SR'" group, with R'" being an alkyl group of 1 to 6 carbon atoms, substituted, or not, by one or more halogen atoms;

c) $R_2$ is:
   a linear or branched alkyl group of 1 to 6 carbon atoms, substituted or not, by:
   an —$OR_6$, —$SR_6$ or —$SOR_6$ group, with $R_6$ being hydrogen, a linear or branched alkyl group of 1 to 4 carbons, a phenyl or benzyl group;
   a —$CO_2R_7$ group, with $R_7$ being hydrogen, a linear or branched alkyl group comprising 2 to 4 carbon atoms, or a benzyl group;
   an —$NR_8R_9$ group, with $R_8$ and $R_9$ being, independently, hydrogen, a linear or branched alkyl group of 1 to 4 carbon atoms, a phenyl or benzyl group, or with —$NR_8R_9$ taken together being a saturated 5- or 6-membered heterocycle comprising one or more heteroatoms selected from N or O
   a carboxamide group —$CONR_8R_9$, with —$NR_8R_9$ as defined above;
   a phenyl group, substituted, or not, by one or more halogens selected from fluorine or bromine, an alkoxy group —$OR_6$, with $R_6$ having the same definition as above, or by a phenyl group;
   an aromatic 5- or 6-membered heterocycle comprising 1 or 2 heteroatoms selected from oxygen, nitrogen and sulfur; or
   a saturated 5- or 6-membered cyclic or heterocyclic compound comprising 1 or 2 heteroatoms selected from oxygen, nitrogen and sulfur;
   a saturated 5- or 6-membered cyclic or heterocyclic compound comprising 1 or 2 heteroatoms selected from oxygen, nitrogen and sulfur; or
   a phenyl group, substituted or not, by one or more halogens selected from fluorine or bromine, or by an —$OR_5$ group with $R_5$ having the same definition as above;
   and $R_3$ is hydrogen; or
   $R_2$ and $R_3$ are identical and are a linear or branched alkyl group of 1 to 6 carbon atoms; or
   —$C(R_2)(R_3)$— taken together is:
   a saturated 5-membered cyclic compound fused, or not, to an aromatic ring;
   a saturated 6-membered cyclic compound; or
   a saturated 6-membered heterocyclic compound comprising 1 heteroatom, at the 4-position, selected from oxygen, nitrogen and sulfur, wherein when the heteroatom is nitrogen, the nitrogen is substituted, or not, by an alkyl group of 1 to 6 carbon atoms, a phenyl, benzyl or alkanoyl group;

d) $R_4$ is a linear or branched alkyl group of 1 to 6 carbon atoms substituted by:
  a phenyl group; or
  a phenyl group substituted by:
    one or more halogens selected from fluorine or bromine;
  a phenyl or thienyl group;
e) $R_5$ is:
  a hydroxyl group;
  an —$NR_8R_9$ group, with $R_8$ and $R_9$ being, independently, hydrogen, a linear or branched alkyl group of 1 to 4 carbon atoms, a phenyl or benzyl group, or with —$NR_8R_9$ taken together being a 5- or 6-membered heterocycle, comprising one or more heteroatoms selected from N or O;
  an alkoxy group —$OR_{10}$, with $R_{10}$ being:
    a linear or branched alkyl group, comprised of 2 to 6 carbon atoms;
    a benzyl group;
    a —$CHR_{11}$—$COOR_{12}$, —$CHR_{11}$—O—C(=O)$R_{12}$, —$CHR_{11}$—C(=O)—$OR_{12}$ group wherein $R_{11}$ and $R_{12}$ are, independently, a linear or branched alkyl group of 1 to 6 carbon atoms.

2. The compound according to claim 1, wherein $R_2$ is a linear or branched alkyl group of 1 to 6 carbon atoms or a linear or branched alkyl group of 1 to 6 carbon atoms substituted by:
  a phenyl group;
  a phenyl group substituted by one or more halogens selected from fluorine or bromine;
  an aromatic 5- or 6-membered heterocycle comprising 1 or 2 heteroatoms selected from oxygen, nitrogen and sulfur; or
  a saturated 5- or 6-membered cyclic or heterocyclic compound comprising 1 or 2 heteroatoms selected from oxygen, nitrogen and sulfur;
  and $R_3$ is hydrogen, or
  $R_2$ and $R_3$ are identical and are a linear or branched alkyl group of 1 to 6 carbon atoms,
  or
  —C($R_2$)($R_3$)— taken together is:
  a saturated 5-membered cyclic compound;
  a saturated 5-membered cyclic compound fused to an aromatic ring;
  a saturated 6-membered cyclic compound; or
  a saturated 6-membered heterocyclic compound comprising 1 heteroatom, at the 4-position, selected from oxygen, nitrogen and sulfur.

3. The compound according to claim 1, wherein $R_5$ is a hydroxyl.

4. The compound according to claim 1, wherein:
a) $R_1$ is selected from a group consisting of —$CH_2CH_2SCH_3$, —$CH_2CH_2SOCH_3$, and —$CH_2CH_2CH_2CH_3$;
b) $R_2$ is a linear or branched alkyl group of 1 to 6 carbon atoms or a linear or branched alkyl group of 1 to 6 carbon atoms substituted by:
  a phenyl group;
  a phenyl group substituted by one or more halogens selected from fluorine or bromine;
  an aromatic 5- or 6-membered heterocycle comprising 1 or 2 heteroatoms selected from oxygen, nitrogen and sulfur; or
  a saturated 5- or 6-membered cyclic or heterocyclic compound comprising 1 or 2 heteroatoms selected from oxygen, nitrogen and sulfur;
  and $R_3$ is hydrogen, or
  $R_2$ and $R_3$ are identical and are a linear or branched alkyl group of 1 to 6 carbon atoms; or
  —C($R_2$)($R_3$)— taken together is:
  a saturated 5-membered cyclic compound;
  a saturated 5-membered cyclic compound fused to an aromatic ring;
  a saturated 6-membered cyclic compound; or
  a saturated 6-membered heterocyclic compound comprising 1 heteroatom, at the 4-position, selected from oxygen, nitrogen and sulfur;
c) $R_5$ is a hydroxyl group.

5. The compound according to claim 1, wherein $R_2$ is an isobutyl group or a methyl group substituted by:
  a phenyl group;
  a phenyl group substituted at the 4-position by a halogen selected from fluorine or bromine; or
  a phenyl group substituted at the 4-position by a phenyl group;
  and $R_3$ is hydrogen, or
  $R_2$ and $R_3$ are identical and are a methyl or ethyl group, or
  —C($R_2$)($R_3$)— are together:
  a saturated 5- or 6-membered cyclic group; or
  a saturated 5-membered cyclic group fused to an aromatic ring.

6. The compound according to claim 1, wherein $R_4$ is an alkyl group with one carbon substituted by:
  a phenyl group;
  a phenyl group substituted at the 4-position by a halogen selected from fluorine or bromine; or
  a phenyl group substituted at the 4-position by a phenyl group.

7. The compound according to claim 1, wherein:
$R_2$=$CH_2Ph$; $R_3$=H; $R_4$=$CH_2Ph$; or
$R_2$=iBu; $R_3$=H; $R_4$=$CH_2$(4-Br-Ph); or
$R_2$=$CH_2$(4-Br-Ph); $R_3$=H; $R_4$=$CH_2$(4-Br-Ph); or
$R_2$=$CH_2$(4-Br-Ph); $R_3$=H; $R_4$=$CH_2Ph$;
$R_2$=$CH_2Ph$; $R_3$=H; $R_4$=$CH_2$(4-Br-Ph); or
$R_2$=$CH_2$(4-Ph-Ph); $R_3$=H; $R_4$=$CH_2$(4-Br-Ph); or
$R_2$=$CH_3$; $R_3$=$CH_3$; $R_4$=$CH_2$(4-Br-Ph); or
$R_2$=$C_2H_5$; $R_3$=$C_2H_5$; $R_4$=$CH_2$(4-Br-Ph); or
C($R_2$)($R_3$)=$C_5H_8$; $R_4$=$CH_2$(4-Br-Ph); or
C($R_2$)($R_3$)=$C_6H_{10}$; $R_4$=$CH_2$(4-Br-Ph); or
C($R_2$)($R_3$)=$C_9H_8$; $R_4$=$CH_2$(4-Br-Ph); or
C($R_2$)($R_3$)=$C_6H_{10}$; $R_4$=$CH_2$(4-Ph-Ph); or
C($R_2$)($R_3$)=$C_5H_8$; $R_4$=$CH_2$(4-Br-Ph); or
C($R_2$)($R_3$)=$C_9H_8$; $R_4$=$CH_2$(4-Ph-Ph).

8. The compound according to claim 1, wherein $R_1$ is selected from a group consisting of —$CH_2CH_2SCH_3$, $CH_2CH_2SOCH_3$, and —$CH_2CH_2CH_2CH_3$.

9. The compound according to claim 1 wherein:
$R_1$=$CH_2CH_2SCH_3$; $R_2$=$CH_2CH(CH_3)_2$; $R_3$=H; $R_4$=$CH_2$(4-Br-Ph);
$R_1$=$CH_2CH_2CH_2CH_3$; $R_2$=$CH_2CH(CH_3)_2$; $R_3$=H; $R_4$=$CH_2$(4-Br-Ph);
$R_1$=$CH_2CH_2SOCH_3$; $R_2$=$CH_2CH(CH_3)_2$; $R_3$=H; $R_4$=$CH_2$(4-Br-Ph);
$R_1$=$CH_2CH_2CH_2CH_3$; C($R_2$)($R_3$)=Cyclohexyl; $R_4$=$CH_2$(4-Br-Ph);
$R_1$=$CH_2CH_2SCH_3$; C($R_2$)($R_3$)=Cyclohexyl; $R_4$=$CH_2$(4-Ph-Ph); or
$R_1$=$CH_2CH_2CH_2CH_3$; C($R_2$)($R_3$)=Cyclohexyl; $R_4$=$CH_2$(4-Ph-Ph).

10. The compound according to claim 1, formulated as a drug.

11. The compound according to claim 10, formulated as an analgesic, anxiolytic, antidepressant or anti-inflammatory.

12. A pharmaceutical composition comprising at least one compound of formula (1)

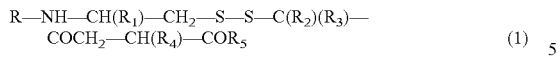

wherein
f) R is:
  hydrogen; or
  an alkoxyalkylcarbonyl group R'C(O)OCH(R")OC(O)— where R' and R" are, independently, an alkyl group containing 1 to 6 carbon atoms;
g) $R_1$ is a linear or branched alkyl group of 1 to 6 carbon atoms, substituted, or not, by an —OR''', —SOR''' or —SR''' group, with R''' being an alkyl group of 1 to 6 carbon atoms, substituted, or not, by one or more halogen atoms;
h) $R_2$ is:
  a linear or branched alkyl group of 1 to 6 carbon atoms, substituted or not, by:
    an —$OR_6$, —$SR_6$ or —$SOR_6$ group, with $R_6$ being hydrogen, a linear or branched alkyl group of 1 to 4 carbons, a phenyl or benzyl group;
    a —$CO_2R_7$ group, with $R_7$ being hydrogen, a linear or branched alkyl group comprising 2 to 4 carbon atoms, or a benzyl group;
    an —$NR_8R_9$ group, with $R_8$ and $R_9$ being, independently, hydrogen, a linear or branched alkyl group of 1 to 4 carbon atoms, a phenyl or benzyl group, or with —$NR_8R_9$ taken together being a saturated 5- or 6-membered heterocycle comprising one or more heteroatoms selected from N or O;
    a carboxamide group —$CONR_8R_9$, with —$NR_8R_9$ as defined above;
    a phenyl group, substituted, or not, by one or more halogens selected from fluorine or bromine, an alkoxy group —$OR_6$, with $R_6$ having the same definition as above, or by a phenyl group;
    an aromatic 5- or 6-membered heterocycle comprising 1 or 2 heteroatoms selected from oxygen, nitrogen and sulfur; or
    a saturated 5- or 6-membered cyclic or heterocyclic compound comprising 1 or 2 heteroatoms selected from oxygen, nitrogen and sulfur;
  a saturated 5- or 6-membered cyclic or heterocyclic compound comprising 1 or 2 heteroatoms selected from oxygen, nitrogen and sulfur; or
  a phenyl group, substituted or not, by one or more halogens selected from fluorine or bromine, or by an —$OR_5$ group with $R_5$ having the same definition as above;
and $R_3$ is hydrogen; or
$R_2$ and $R_3$ are identical and are a linear or branched alkyl group of 1 to 6 carbon atoms; or
—$C(R_2)(R_3)$— taken together is:
  a saturated 5-membered cyclic compound fused, or not, to an aromatic ring;
  a saturated 6-membered cyclic compound; or
  a saturated 6-membered heterocyclic compound comprising 1 heteroatom, at the 4-position, selected from oxygen, nitrogen and sulfur, wherein when the heteroatom is nitrogen, the nitrogen is substituted, or not, by an alkyl group of 1 to 6 carbon atoms, a phenyl, benzyl or alkanoyl group;
i) $R_4$ is a linear or branched alkyl group of 1 to 6 carbon atoms substituted by:
  a phenyl group; or
  a phenyl group substituted by:
    one or more halogens selected from fluorine or bromine;
  a phenyl or thienyl group;
j) $R_5$ is:
  a hydroxyl group;
  an —$NR_8R_9$ group, with $R_8$ and $R_9$ being, independently, hydrogen, a linear or branched alkyl group of 1 to 4 carbon atoms, a phenyl or benzyl group, or with —$NR_8R_9$ taken together being a 5- or 6-membered heterocycle, comprising one or more heteroatoms selected from N or O;
  an alkoxy group —$OR_{10}$, with $R_{10}$ being:
    a linear or branched alkyl group, comprised of 2 to 6 carbon atoms;
    a benzyl group; or
    a —$CHR_{11}$—$COOR_{12}$, —$CHR_{11}$—O—C(=O)$R_{12}$, —$CHR_{11}$—C(=O)—$OR_{12}$ group wherein $R_{11}$ and $R_{12}$ are, independently, a linear or branched alkyl group of 1 to 6 carbon atoms; and
at least one pharmaceutically acceptable excipient.

13. The pharmaceutical composition according to claim 12, which is an analgesic, anxiolytic, antidepressant or anti-inflammatory.

14. The pharmaceutical composition according to claim 12, comprising at least one compound selected from the group consisting of morphine, endocannabinoids, and inhibitors of endocannabinoid metabolism, gabapentin, pregabalin, duloxetine and methadone.

15. The pharmaceutical composition according to claim 12, adapted for parenteral, topical, oral, or nasal administration.

16. A method for treating pain, wherein, said method comprising administering, to a patient in need thereof, an effective dose of a compound of formula (1) according to claim 1, or a pharmaceutically acceptable salt thereof.

17. The method of claim 16, further comprising administering an effective amount of at least one compound selected from the group consisting of morphine, endocannabinoids, inhibitors of endocannabinoid metabolism, gabapentin, pregabalin, duloxetine and methadone.

18. The method of claim 16, wherein the compound of formula (1) is administered via parenteral, topical, oral, or nasal route.

19. A method for treating pain, wherein, said method comprising administering, to a patient in need thereof, an effective dose of a composition according to claim 12.

20. The compound according to claim 1, wherein $R_2$ is morpholine or piperidine.

21. The compound according to claim 1, wherein —(C)$(R_2)(R_3)$— taken together is an indanyl ring.

22. The compound according to claim 1, wherein $R_5$ is morpholine or piperidine.

* * * * *